(12) United States Patent
Eckman

(10) Patent No.: US 8,137,402 B2
(45) Date of Patent: *Mar. 20, 2012

(54) VERTEBRAL DEFECT DEVICE

(75) Inventor: Walter W. Eckman, Tupelo, MS (US)

(73) Assignee: Concept Matrix LLC, Orlando, FL (US)

( * ) Notice: Subject to any disclaimer, the term of this patent is extended or adjusted under 35 U.S.C. 154(b) by 311 days.

This patent is subject to a terminal disclaimer.

(21) Appl. No.: 12/141,702

(22) Filed: Jun. 18, 2008

(65) Prior Publication Data

US 2008/0249629 A1 Oct. 9, 2008

Related U.S. Application Data

(60) Continuation-in-part of application No. 11/463,056, filed on Aug. 8, 2006, now Pat. No. 7,674,295, which is a continuation-in-part of application No. 10/988,830, filed on Nov. 15, 2004, now Pat. No. 7,534,267, which is a division of application No. 10/345,591, filed on Jan. 16, 2003, now Pat. No. 7,105,023.

(60) Provisional application No. 60/369,510, filed on Apr. 2, 2002, provisional application No. 60/349,730, filed on Jan. 17, 2002.

(51) Int. Cl.
*A61F 2/44* (2006.01)
(52) U.S. Cl. ............ 623/17.11; 623/17.16; 606/246
(58) Field of Classification Search ............... 623/17.11, 623/17.16; 606/246
See application file for complete search history.

(56) References Cited

U.S. PATENT DOCUMENTS

| 4,349,921 A | 9/1982 | Kuntz |
| 4,545,374 A | 10/1985 | Jacobson |
| 4,936,848 A | 6/1990 | Bagby |

(Continued)

FOREIGN PATENT DOCUMENTS

EP 1099429 A1 5/2001

(Continued)

OTHER PUBLICATIONS

Office Action, dated Jan. 26, 2005, in related U.S. Appl. No. 10/345,591.

(Continued)

*Primary Examiner* — David Isabella
*Assistant Examiner* — Javier Blanco
(74) *Attorney, Agent, or Firm* — Panitch Schwarze Belisario & Nadel LLP

(57) ABSTRACT

A vertebral defect device for insertion into an intervertebral space between a pair of adjacent vertebrae and for assisting in fusion between the adjacent vertebrae includes a rigid body having an distal end, a proximal end, a top, a bottom and a pair of lateral sides. The distal end is tapered in a general direction that extends between the top and the bottom of the body in order to facilitate insertion of the body into the intervertebral space. At least a first arch is proximate the top of the body and extends from the proximal end of the body toward the distal end of the body. The first arch is spaced from both lateral sides of the body. At least a second arch is proximate the bottom of the body and extends from the proximal end toward the distal end. The second arch is spaced from both lateral sides and is generally laterally aligned with the first arch for providing a rigid, generally vertical support.

16 Claims, 14 Drawing Sheets

U.S. PATENT DOCUMENTS

| | | | |
|---|---|---|---|
| 4,961,740 A | 10/1990 | Ray et al. |
| 5,258,031 A | 11/1993 | Salib et al. |
| D356,129 S | 3/1995 | Wolf |
| 5,425,773 A | 6/1995 | Boyd et al. |
| 5,484,437 A | 1/1996 | Michelson |
| 5,522,899 A | 6/1996 | Michelson |
| 5,549,679 A | 8/1996 | Kuslich |
| 5,562,738 A | 10/1996 | Boyd et al. |
| 5,571,189 A | 11/1996 | Kuslich |
| D377,095 S | 12/1996 | Michelson |
| D377,096 S | 12/1996 | Michelson |
| D377,527 S | 1/1997 | Michelson |
| 5,593,409 A | 1/1997 | Michelson |
| 5,609,635 A | 3/1997 | Michelson |
| 5,609,636 A | 3/1997 | Kohrs et al. |
| 5,645,596 A | 7/1997 | Kim et al. |
| 5,653,761 A | 8/1997 | Pasharodi |
| 5,669,909 A | 9/1997 | Zdeblick et al. |
| 5,674,296 A | 10/1997 | Bryan et al. |
| 5,702,449 A | 12/1997 | McKay |
| 5,766,252 A | 6/1998 | Henry et al. |
| 5,776,199 A | 7/1998 | Michelson |
| 5,785,710 A | 7/1998 | Michelson |
| 5,888,226 A | 3/1999 | Rogozinski |
| 5,906,616 A | 5/1999 | Pavlov et al. |
| 5,980,522 A | 11/1999 | Koros et al. |
| 5,984,967 A | 11/1999 | Zdeblick et al. |
| 6,039,762 A | 3/2000 | McKay |
| D425,989 S | 5/2000 | Michelson |
| 6,102,950 A | 8/2000 | Vaccaro |
| 6,113,637 A | 9/2000 | Gill et al. |
| 6,136,031 A | 10/2000 | Middleton |
| 6,174,334 B1 | 1/2001 | Suddaby |
| 6,193,757 B1 | 2/2001 | Foley et al. |
| 6,210,412 B1 | 4/2001 | Michelson |
| 6,245,108 B1 | 6/2001 | Biscup |
| 6,270,528 B1 | 8/2001 | McKay |
| 6,309,421 B1 | 10/2001 | Pisharodi |
| 6,419,705 B1 | 7/2002 | Erickson |
| 6,425,920 B1 | 7/2002 | Hamada |
| 6,447,544 B1 | 9/2002 | Michelson |
| 6,447,547 B1 | 9/2002 | Michelson |
| 6,454,805 B1 | 9/2002 | Baccelli et al. |
| 6,468,311 B2 | 10/2002 | Boyd et al. |
| 6,478,822 B1 | 11/2002 | Leroux et al. |
| 6,478,823 B1 | 11/2002 | Michelson |
| 6,520,991 B2 | 2/2003 | Huene |
| 6,558,424 B2 | 5/2003 | Thalgott |
| 6,582,433 B2 | 6/2003 | Yun |
| 6,607,558 B2 | 8/2003 | Kuras |
| 6,648,917 B2 | 11/2003 | Gerbec et al. |
| 6,824,564 B2 * | 11/2004 | Crozet | 623/17.11 |
| 6,852,129 B2 | 2/2005 | Gerbec et al. |
| 6,855,168 B2 | 2/2005 | Crozet |
| 6,902,581 B2 | 6/2005 | Walkenhorst et al. |
| 6,923,810 B1 | 8/2005 | Michelson |
| 7,011,684 B2 | 3/2006 | Eckman |
| 7,046,714 B2 | 5/2006 | Nicolaescu et al. |
| 7,112,222 B2 * | 9/2006 | Fraser et al. | 623/17.11 |
| 7,125,425 B2 | 10/2006 | Foley et al. |
| 7,156,877 B2 | 1/2007 | Lotz et al. |
| 7,163,561 B2 | 1/2007 | Michelson |
| 7,503,933 B2 | 3/2009 | Michelson |
| 2001/0018614 A1 | 8/2001 | Bianchi |
| 2002/0116009 A1 | 8/2002 | Fraser et al. |
| 2003/0004576 A1 | 1/2003 | Thalgott |
| 2004/0054412 A1 | 3/2004 | Gerbec et al. |
| 2004/0254644 A1 | 12/2004 | Taylor |
| 2005/0004672 A1 | 1/2005 | Pafford et al. |
| 2005/0159816 A1 * | 7/2005 | Walkenhorst et al. | 623/17.11 |
| 2008/0015581 A1 | 1/2008 | Eckman |
| 2008/0015695 A1 | 1/2008 | Eckman |

FOREIGN PATENT DOCUMENTS

| | | |
|---|---|---|
| EP | 1112753 B1 | 7/2001 |
| EP | 1849437 A2 * | 10/2007 |
| FR | 2742044 A1 | 6/1997 |
| FR | 2762779 A1 | 6/1998 |
| FR | 2794967 A1 | 12/2000 |
| GB | 2097594 A | 11/1982 |
| WO | 9640014 A1 | 12/1996 |
| WO | 9714377 A1 | 4/1997 |
| WO | 9932054 A1 | 7/1999 |

OTHER PUBLICATIONS

Office Action, dated Nov. 30, 2005, in related U.S. Appl. No. 10/345,591.

Office Action, dated Jul. 2, 2008, in related U.S. Appl. No. 10/988,830.

Int'l Search Report, dated Jun. 30, 2003, in related PCT/US03/01508.

Office Action, dated Jan. 27, 2009, in related European Patent Application No. 03731980.3.

Depraetere, P., et al., "Interbody Cages in PLIF Surgery: A Multicentric Report", Journal of Musculoskeletal Research, vol. 2, No. 1 (1998) 9-14.

Helmut D. Link, et al., "Link SB Charite Artificial Disc: History, Design & Biomechanics", Spinal Restabilization Procedures. Edited by D. L. Kaech and J.R. Jinkins, 297-298 (2002), Berlin, Germany.

McAfee, Paul C., "Artificial Disc Prosthesis: The Link SB Charite III", Spinal Restabilization Procedures, edited by D. L. Kaech and J.R. Jinkins, 299-301 (2002) Towson, MD.

"Prodisc" Brochure, Spine Solutions, New York, NJ.

"Link SB Charite Artificial Disc" Brochure, Maintaining Natural Mobility, Link Spine Group, Branford, Connecticut.

"Prodisc" Brochure, Spine Solutions: The Non-Fusion Technology Company.

Spine Arthroplasty, Spine Industry Analysis Series, Viscogliosi Bros., LLC, Nov. 2001.

European Patent Office, Supplementary European Search Report, Feb. 18, 2008.

Office Action, dated May 25, 2010, in EP Application No. 03731980.3.

Office Action dated Jul. 23, 2009.

Office Action dated May 29, 2009.

* cited by examiner

VERTEBRAL DEFECT DEVICE

CROSS-REFERENCE TO RELATED APPLICATIONS

This application is a continuation-in-part of Ser. No. 11/463,056, now U.S. Patent No. 7,674,295 B2 filed Aug. 8, 2006, entitled "Vertebral Defect Device," which is a continuation-in-part of Ser. No. 10/988,830, now U.S. Pat. No. 7,534,267 B2 filed Nov. 15, 2004, entitled "Methods of Installing a Vertebral Defect Device," which is a divisional of Ser. No. 10/345,591, now U.S. Pat. No. 7,105,023 B2, filed Jan. 16, 2003 entitled "Vertebral Defect Device." This application claims the benefit of U.S. Provisional Patent Application No. 60/369,510 filed Apr. 2, 2002, entitled "Intervertebral Fusion Cage" and U.S. Provisional Patent Application No. 60/349,730 filed Jan. 17, 2002, entitled "Intervertebral Fusion Cage."

BACKGROUND OF THE INVENTION

The present invention relates generally to vertebral fixation or defect devices, and more particularly, to an intervertebral defect device for insertion into an intervertebral space using minimally invasive surgical techniques.

As shown in prior art FIGS. 1A-4, it is known in the prior art that the spine 120, also known as the spinal column or vertebral column, supports the upper body, allows head, neck, and trunk motion, and includes twenty-four moveable vertebrae 100 including seven cervical vertebrae 102, twelve thoracic vertebrae 104, and five lumbar vertebrae 106, which extend from the skull to the sacrum. In FIGS. 1A and 3, the directional arrow 101a is pointing in the posterior direction and the directional arrow 101b is pointing in the anterior direction.

Referring to FIG. 3, with the exception of the first, uppermost cervical vertebra 102, each vertebra 100 has a vertebral body 103, a lamina 110, a spinous process 105, as well as facet structures 114 (which form facet joints), two transverse processes 116, and two pedicles 118, one on each side. Each individual vertebra 100 has a large foramen 111, which forms the spinal canal 128 (FIG. 2) when the vertebrae 100 are in their normal anatomical position forming the spine 120. The spinal cord and major nerve fiber groups pass through and are protected by the spinal canal 128. A strong fibrous membrane, the dura mater (not shown), also known as the dura, surrounds the spinal cord, nerve fibers, and fluid in the spinal canal 128.

Referring to FIG. 4, each pair of adjacent vertebrae 100 along with interconnecting soft tissues and an intervertebral disk 121 constitutes a motion segment 122, also known as a functional spinal unit. The combined motions of many such motion segments 122 constitute overall spinal motion at any one time. The intervertebral disk 121 resides in the space between adjacent vertebral bodies, the intervertebral space 130, also known as the interbody space or disk space. The level of each particular intervertebral space 130 and intervertebral disk 121 is identified by naming the vertebrae 100 superior and inferior to it, for example $L^{IV-V}$ in the case of the intervertebral space 130 and intervertebral disk 121 between the fourth and fifth lumbar vertebrae $L^{IV}$, $L^{V}$.

Referring to FIGS. 2 and 4, the superior surface 100a and the inferior surface 100b (FIG. 2) of each the lumbar and thoracic vertebral bodies 104, 106 are concave (the shape of the vertebral space 130 shown in phantom in FIG. 4). Owing to the shapes of the inferior and superior surfaces 100a, 100b of the vertebral bodies 104, 106, the lumbar and thoracic intervertebral spaces 130 and intervertebral disks 121 are biconvex.

Situations arise in which one or more motion segments 122 do not have adequate support or stability, which can lead to pain, deformity, stenosis of spinal canal or neuroforamina, and impairment or loss of nerve function. In some cases, surgical spine fusion is considered. Spine fusion is a process of growing bone between two or more adjacent vertebrae 100 such that the adjacent vertebrae 100 of a motion segment 122 will move only in unison. This process involves placing bone, or material to guide or stimulate bone growth, in proximity to exposed bone of the vertebrae 100, and then allowing time for new bone to grow and form a structurally strong connection, or fusion, between the adjacent vertebrae 100. The earliest such procedures took place approximately a century ago, and the procedures have developed over many years, including various attempts to fuse posterior structures of the spine 120 such as the spinous process 105, lamina 110, facet joints 114, and transverse processes 116.

Recently, there has been more interest in fusion involving bone growth directly between adjacent vertebral bodies 100 within the intervertebral spaces 130. Large amounts of well vascularized bone are in close proximity, there is a large surface area available, and the inherent compression force applied between vertebral bodies 100 by muscle tension and the upright position of the human body enhances bone formation and strength. The intervertebral disk space 130 has therefore become a major focus in interbody fusion surgery. During such surgery, the disk space 130 is cleared as much as possible, and cartilage and abnormal surface bone, also known as endplate bone, from adjacent vertebral bodies 100 is removed, after which material is placed in the space to promote fusion. However, loose bone fragments do not provide structural support and therefore fusion is often unsuccessful. Structural bone grafts from the patient or donors have been successful, but may give rise to pain and complications if from the patient, and the additional risk of disease transmission if from a donor.

Vertebral defect devices are increasingly used to assist with fusion between vertebral bodies. Such devices need sufficient strength to provide support to prevent excessive collapse of the vertebral space 130 between vertebrae 100 which could result in stenosis of the spinal canal or neuroforamina, progressive deformity, impairment or loss of nerve function, or pain. Such devices also preferably provide at least one compartment to fill with bone, or material which assists in bone growth, in order to maintain close contact with vertebral bone as new bone is encouraged to bridge across the space 130 involved.

Referring to FIG. 3, which shows a single plan view of a vertebra 100, it is known in the art that vertebral defect devices can be inserted from several directions (indicated by arrowed lines). Typically, vertebral defect devices are inserted through anterior or lateral approaches E, F. Anterior approaches E allow more access to the disk space, but require more destruction of the annulus. In the lumbar spine 106, bilateral placement of devices has sometimes been necessary to achieve adequate stability.

Lumbar surgery is experiencing an evolution to minimally invasive surgery by accessing the intervertebral disk space 130 through a posterior approach A, B, C, D. This trend has led to the need for devices that can be inserted through small portals or working channels, usually through one small incision from the posterior direction 101a laterally spaced from spine 120. In lumbar fusion, vertebral devices should assist with rapid fixation to minimize the need for extensive additional fixation with bone screws, rods, and plates. Surgeons generally prefer posterior approaches for lumbar spine procedures due to the morbidity of anterior approaches, which also cause adhesion of major vessels and make repeat anterior surgery very dangerous and even life threatening. When posterior lumbar fusion is performed, there is an opportunity to approach the spine 120 through the neuroforamina 124 (FIG. 4) and insert the vertebral defect devices through a small space free of vital structures which is located lateral to the dura in the spinal canal 128, medial to the large nerve root passing through the neuroforamina 124, and bordered inferiorly or caudally by the pedicle 118 of the vertebra 100 below the involved disk space 130. The distance between peripheral edges of the vertebrae 100 at the disk space 130 is often small so that entry of devices has required considerable bone removal to safely impact devices into the disk space 130. If a device with a distal end of 3 mm or larger in height or transverse dimension is impacted into the disk space 130, it will frequently displace medially or laterally, and involve nerve structures. When working through a small portal or working channel, it is difficult to see this displacement, which makes some devices dangerous in this regard.

Conventional vertebral devices adapted for bilateral surgery do not lend themselves to being used in minimally invasive surgery. When inserting a conventional vertebral device, a distraction tool is used to separate adjacent vertebrae 100 and open the disk space 130 on one side of the spine 120 to allow insertion of the vertebral device on the other side of the spine 120. Alternatively, pedicle screws on one or both sides of the spine 120 may be used with a distraction instrument to spread open the disc space 130 for insertion of one or more vertebral devices. Cylindrically-shaped devices, inserted through posterior and transforaminal approaches A, B, C, D are associated with increased potential for nerve root or dural injury, particularly when drill tubes and reamers are used to prepare the disk space 130 for fusion.

What is needed is a vertebral defect device used in minimally invasive surgery that is designed to achieve rapid fixation while preventing excessive subsidence. The device should reduce the potential for neural injury during insertion, and reduce or eliminate the need for bilateral lumbar pedicle screws. The device should have excellent support strength, allow for the insertion of fusion material within the device and allow for viewing of the bone growth. The device is preferably placed through an incision and directly into the disk space without manual or mechanical separation of the vertebrae.

BRIEF SUMMARY OF THE INVENTION

Briefly stated, the present invention is directed to a vertebral defect device for insertion into an intervertebral space between a pair of adjacent vertebrae and for assisting in fusion between the adjacent vertebrae. The vertebral defect device includes a rigid body having an distal end, a proximal end, a top, a bottom and a pair of lateral sides. The distal end is tapered in a general direction that extends between the top and the bottom of the body in order to facilitate insertion of the body into the intervertebral space. At least a first arch is proximate the top of the body and extends from the proximal end of the body toward the distal end of the body. The first arch is spaced from both lateral sides of the body. At least a second arch is proximate the bottom of the body and extends from the proximal end toward the distal end. The second arch is spaced from both lateral sides and is generally laterally aligned with the first arch for providing a rigid, generally vertical support.

In another aspect, the present invention is directed to a vertebral defect device for insertion into an intervertebral space between a pair of adjacent vertebrae and for assisting in fusion between the adjacent vertebrae. The vertebral defect device includes a rigid body that has a distal end, a proximal end, a top, a bottom and a pair of lateral sides. The distal end is tapered in a general direction that extends between the top and the bottom of the body in order to facilitate insertion of the body into the intervertebral space. At least two slots extend entirely through the body from the top to the bottom to form at least one rigid support disposed between and at least partially spaced from the lateral sides. The at least two slots have a length that extends between the proximal and distal ends of the body and a width that extends between the lateral sides. The length of the at least two slots is larger than the width.

In another aspect, the present invention is directed to a vertebral defect device for insertion into an intervertebral space between a pair of adjacent vertebrae and for assisting in fusion between the adjacent vertebrae. The vertebral defect device includes a rigid body that has a tapered distal tip to facilitate insertion of the body into the intervertebral space and first and second lateral sidewalls that are spaced from each other and extend proximally from the distal tip. At least one support plate extends proximally from the distal tip of the body and spaced from and between the lateral sidewalls of the body to form a first slot between the first lateral sidewall and the at least one support plate and a second slot between the second lateral sidewall and the at least one support plate. A side aperture extends laterally through at least one of the first and second lateral sidewalls and through the at least one support plate to form a central cavity.

BRIEF DESCRIPTION OF THE SEVERAL VIEWS OF THE DRAWINGS

The foregoing summary, as well as the following detailed description of preferred embodiments of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown.

In the drawings.

DETAILED DESCRIPTION OF THE INVENTION

Figures 1A, 1B:
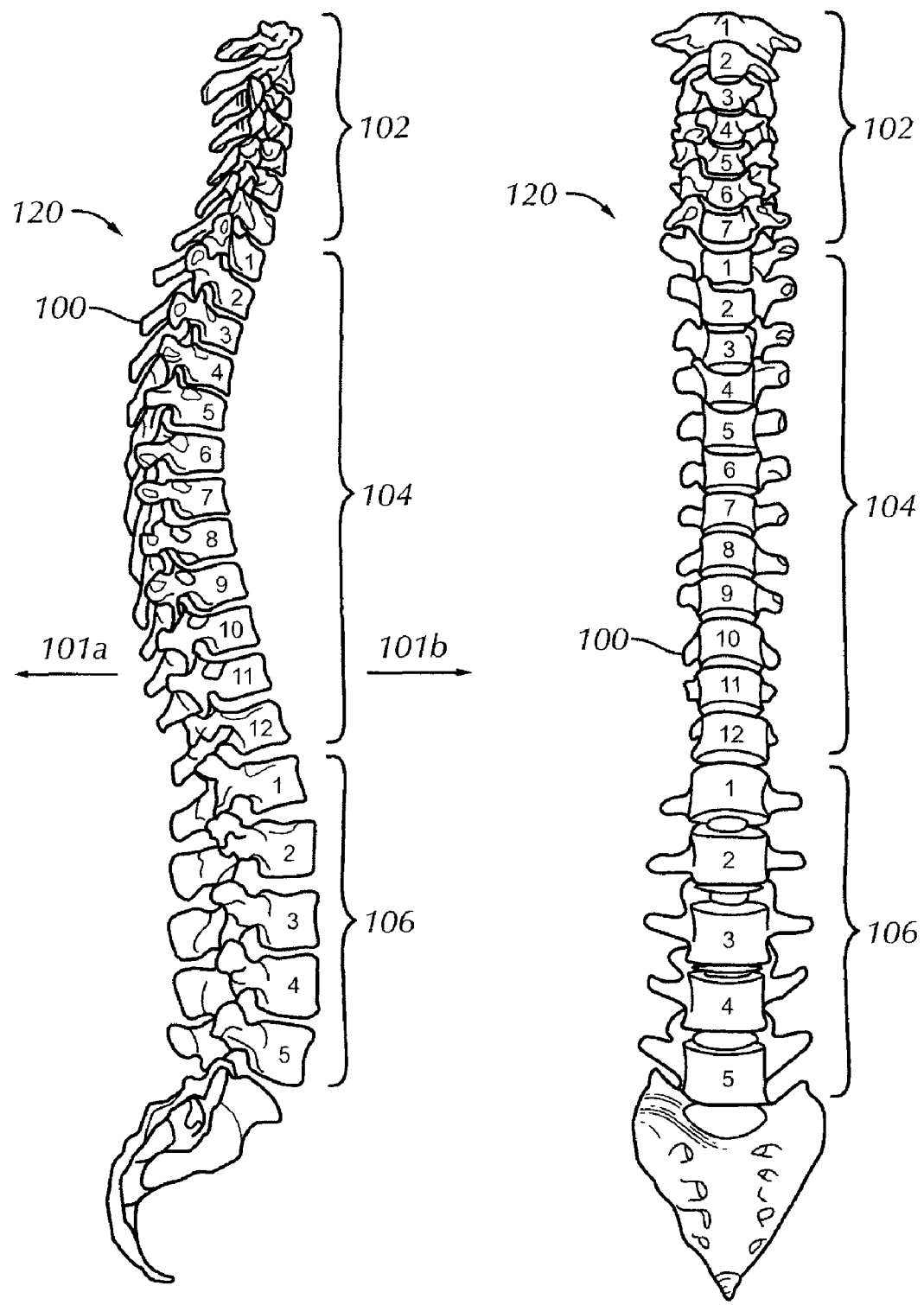
FIG. 1A is a right side elevation view of a human spinal column as is known in the art.
FIG. 1B is a front elevation view of the human spinal column shown in FIG. 1A.
Figure 2:
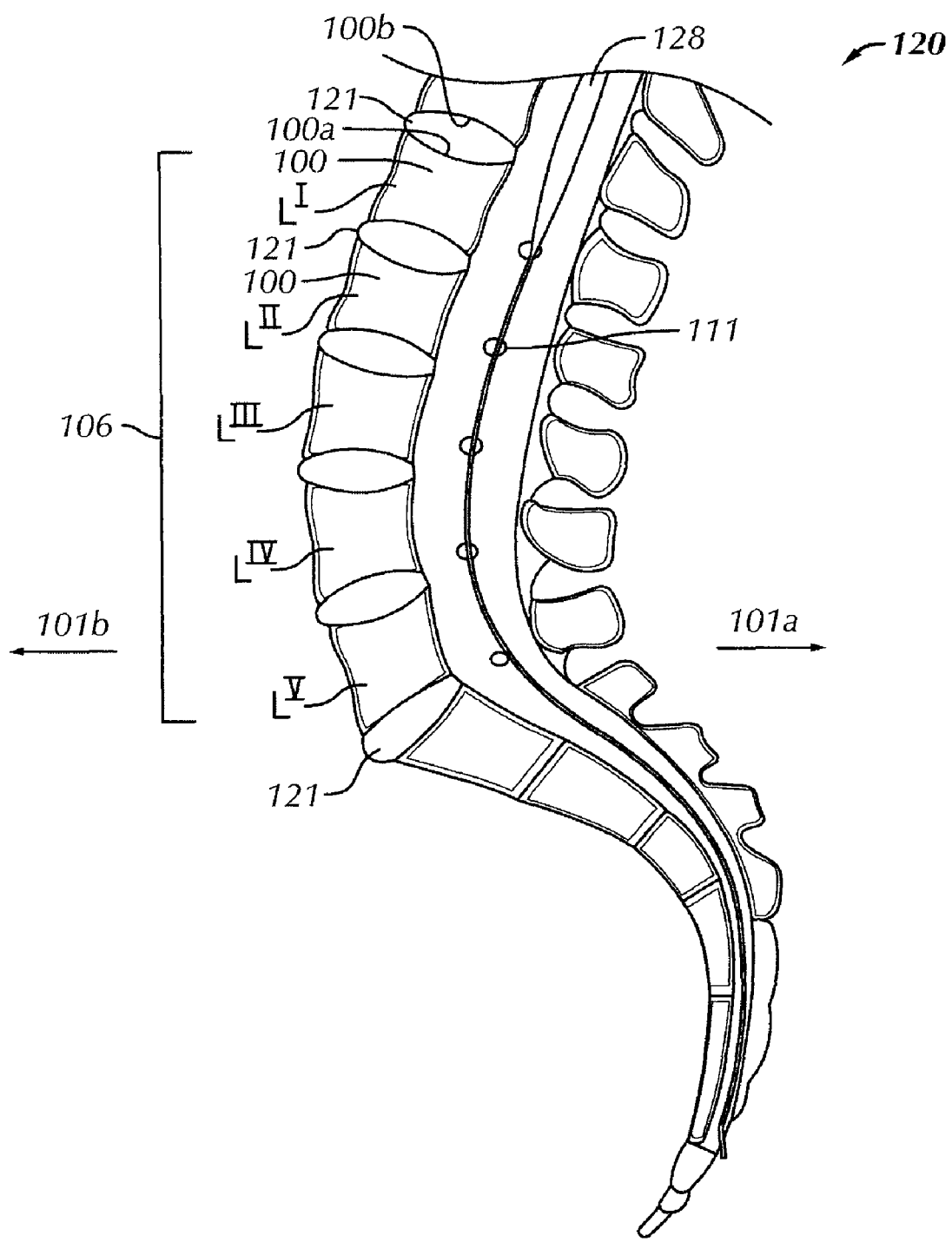
FIG. 2 is a left side sectional view of a portion of the human spine as is known in the art.

Certain terminology is used in the following description for convenience only and is not limiting. The words "right", "left", "lower", and "upper" designate directions in the drawing to which reference is made. The words "inwardly" and "outwardly" refer direction toward and away from, respectively, the geometric center of the vertebral defect device and designated parts thereof. The terminology includes the words above specifically mentioned, derivatives thereof and words of similar import. Additionally, the word "a", as used in the claims and in the corresponding portions of the specification, means "at least one."

The term "vertebral defect device" as used herein may be applicable to a fusion cage device, an interbody device, a partial disk replacement device or a nuclear replacement device without departing from the present invention, and should be construed to broadly encompass any device for use in defects in the spine 120.

Figure 5:
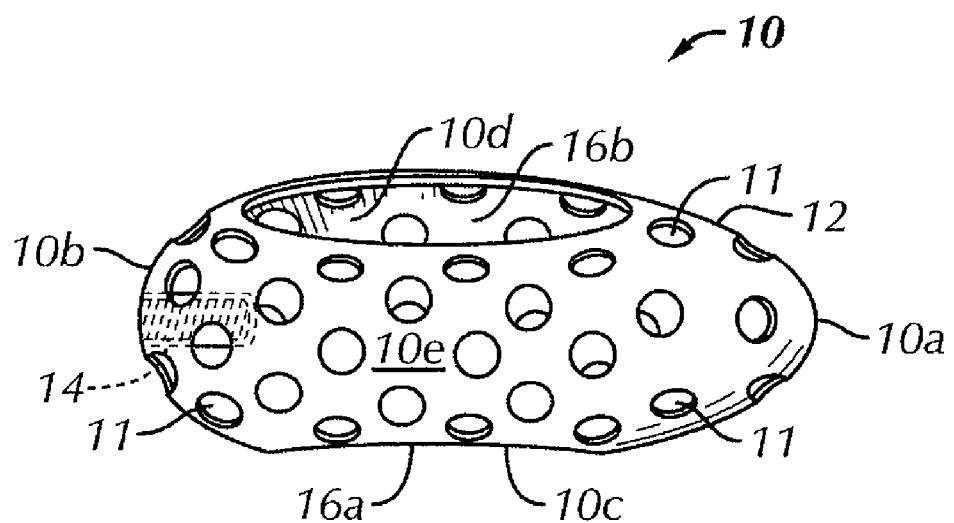
FIG. 5 is a perspective view of a first preferred embodiment of a vertebral defect device in accordance with the present invention.
Figure 6:
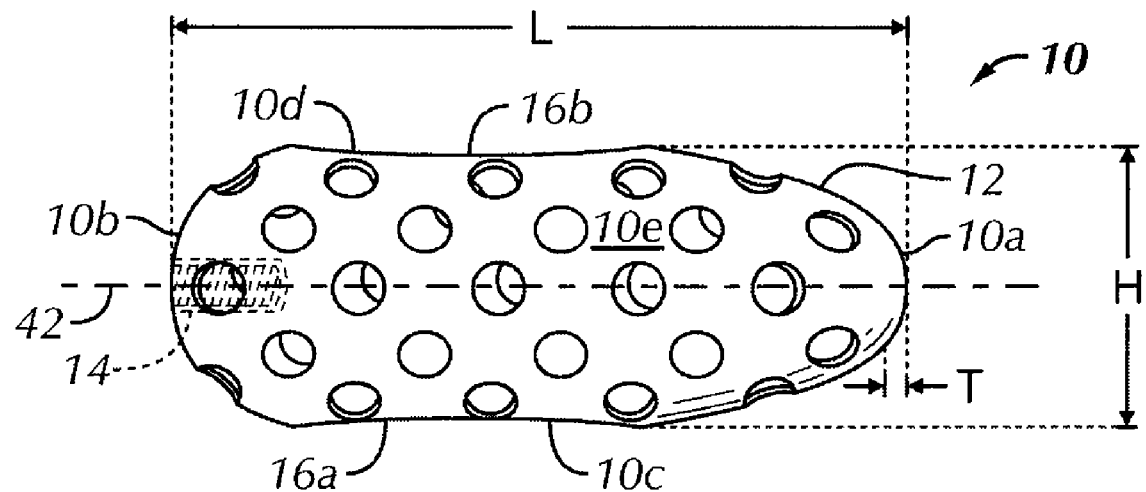
FIG. 6 is a side elevational view of the vertebral defect device of FIG. 5.
Figure 7:
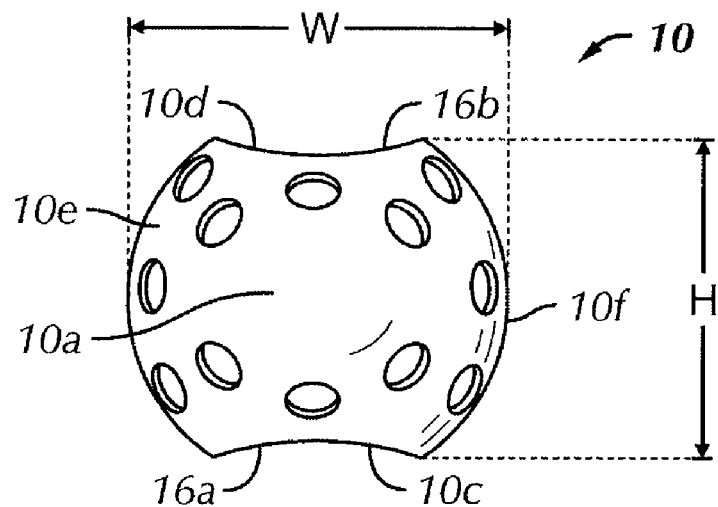
FIG. 7 is a front elevational view of the vertebral defect device of FIG. 5.
Figure 8:
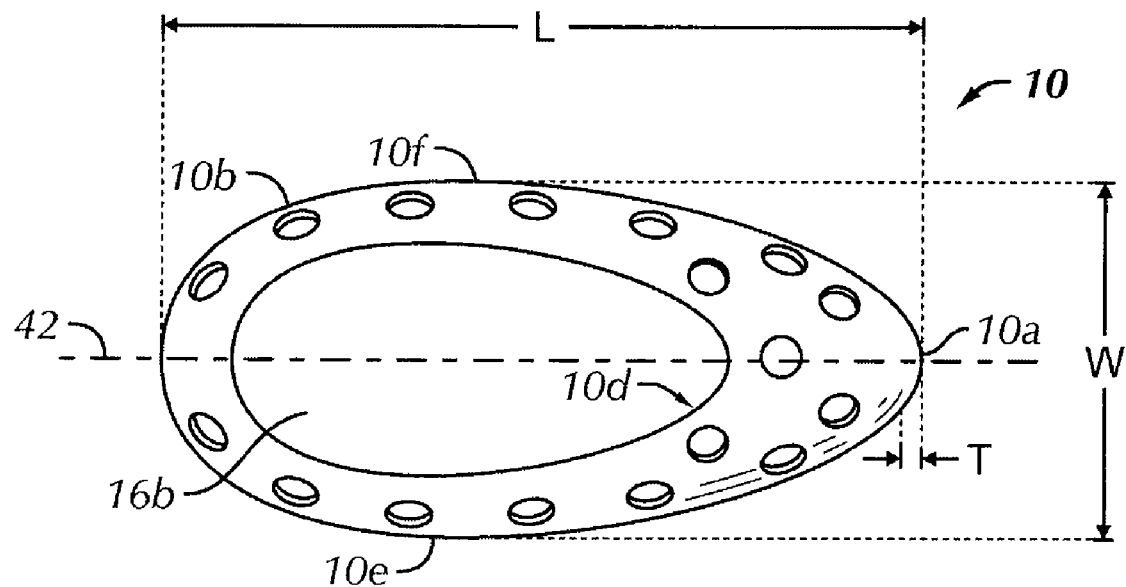
FIG. 8 is a top plan view of the vertebral defect device of FIG. 5.

Referring to the drawings in detail, wherein like reference numerals indicate like elements throughout, there is shown in FIG. 5 a vertebral defect device 10 in accordance with a first preferred embodiment of the present invention. The vertebral defect device 10 has a housing, a convexly-tapered distal end 10a, a convexly-tapered proximal end 10b, a lower wall 10c, an upper wall 10d, a first sidewall 10e, and a second sidewall 10f (FIGS. 7, 8). An outer surface 12 is substantially smooth over the entire surface. The vertebral defect device 10 may be titanium, or any metal or alloy compatible with MRI scanners, synthetic or polymeric materials, composites, ceramic, a biocompatible polymeric material, any biologically absorbable material and the like without departing from the broad inventive scope of the present invention.

The vertebral defect device 10 is generally lens-shaped or ovoid-shaped with rounded or contoured edges on all sides. In particular, the proximal end 10b preferably is rounded but more bluntly-shaped than the distal end 10a which preferably is sloped into a bullet-shaped tip. The proximal end 10b is preferably generally ovoid-shaped. Thus, the distal end 10a has a lesser average radius of curvature than the proximal end 10b. The lower wall 10c and upper wall 10d preferably are generally convex in order to cooperatively mate within the natural concavities of adjacent vertebral bodies 100. Similarly, the first sidewall 10e and second sidewall 10f of the vertebral defect device 10 preferably are similarly convex for similar reasons and to facilitate installation of the vertebral defect device 10 into an intervertebral space 121. The shape of the vertebral defect device 10 is ideally suited for insertion through a small opening, and therefore, the vertebral defect device 10 is well suited for minimally invasive and/or outpatient procedures.

Distributed evenly about the surface 12 of the vertebral defect device 10 are perforations or apertures 11. The apertures 11 are intended to promote rapid bone ingrowth while the vertebral defect device 10 maintains a stiff support structure between the vertebrae 100 during the growth process. While in the presently preferred embodiment, the apertures 11 are shown as circular in shape, the apertures 11 could be any shape including ovals, squares, rectangles, triangles, diamonds, crosses, X-shapes, and the like without departing from the spirit and scope of the invention. But, there need not be apertures 11. Preferably in the first preferred embodiment of the vertebral defect device, the lower wall 10c defines a lower opening 16a and the upper wall 10d of the vertebral defect device 10 defines an upper opening 16b at the point of vertebral contact to encourage successful fusion. The lower opening 16a and the upper opening 16b may be rectangular, circular, elliptical, or the like and may or may not be symmetrically-shaped. The openings 16a, 16b are preferably identically-shaped with respect to one another and are preferably symmetrically-shaped, but need not be. Further, the size of openings 16a and 16b may be varied to accommodate patient variations.

The length L of the vertebral defect device as measured from the distal end 10a to the proximal end 10b preferably is approximately 10-30 mm, depending on the particular intervertebral space 121 in which the vertebral defect device 10 is to be inserted. For example, the intervertebral space between lumbar vertebra $L^{III}$ and lumbar vertebra $L^{IV}$ for an average male would accommodate a vertebral defect device 10 of a length between approximately 25-30 mm. But, the length L of the vertebral defect device 10 could vary from the aforementioned range without departing from the spirit of the invention.

The width W of the vertebral defect device 10 as measured between the first sidewall 10e and the second sidewall 10f of the vertebral defect device 10 will vary from approximately 10 mm to 25 mm depending upon the particular intervertebral space 121 in which the vertebral defect device 10 is to be inserted. For example, the intervertebral space between vertebra $L^{III}$ and vertebra $L^{IV}$ in an average male would accommodate a vertebral defect device 10 having a width W of approximately 15-20 mm. But, the width W of the vertebral defect device 10 could vary from the aforementioned range without departing from the spirit of the invention.

The height H of the vertebral defect device 10 as measured between the upper wall 10d and the lower wall 10c of the vertebral defect device 10 will vary from approximately 5 mm to 25 mm depending upon the particular intervertebral space 121 in which the vertebral defect device 10 is to be inserted. For example, the intervertebral space between vertebra $L^{III}$ and vertebra $L^{IV}$ in an average male would accommodate a vertebral defect device 10 having a height H of approximately 8-16 mm. But, the height H of the vertebral defect device 10 could vary from the aforementioned range without departing from the spirit of the invention.

The overall shape of the vertebral defect device 10 is designed for insertion using minimally invasive techniques through a special portal or channel allowing a procedure to be implemented on an outpatient basis. Further, the vertebral defect device 10 is a self centering device because the shape of the vertebral defect device 10 will encourage it to settle within the natural concavities of adjacent vertebral bodies 100. As such, placement of the vertebral defect device 10 is much faster than that of prior art devices, thereby effectively reducing the duration of a procedure and the associated risks therewith. The smooth contour and edges of the vertebral defect device 10 provide for a safe and easy entrance into the intervertebral space 121.

The convex, bullet-like shape of the distal end 10a of the vertebral defect device 10 will allow it to be driven into the intervertebral space by merely temporarily distracting the vertebrae with minimal removal of the vertebral rim or annulus (not shown clearly) at the point of entry, thereby reducing the chance of dislodging the device post-surgery. Additionally, the self-centering feature of the vertebral defect device 10 will allow rapid settling of the vertebral defect device 10 into adjacent bone to promote rapid bone ingrowth while retention of most of the annulus and peripheral rim of the bodies (vertebrae) would provide good load sharing support to prevent excessive subsidence, where subsidence results from the natural settling of intervertebral matter into a softer central portion of the vertebral bodies 103.

Figure 11:
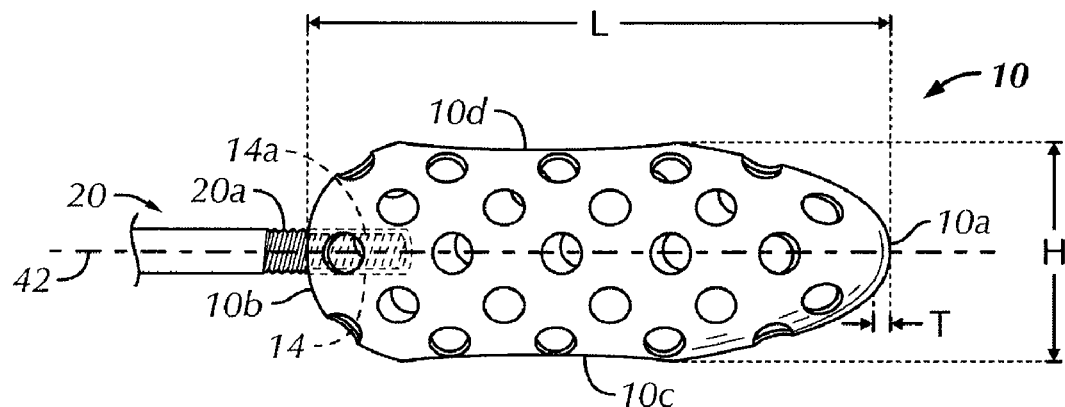
FIG. 11 is a side elevational view of the vertebral defect device of FIG. 5 connected to a first preferred embodiment of an insertion tool in accordance with present invention.

FIG. 11 shows the vertebral defect device 10 of the first preferred embodiment with a first preferred embodiment of a specially designed insertion tool 20. The insertion tool 20 is threaded into a socket 14 in the proximal end of the vertebral defect device 10. The socket 14 is provided with female threads 14a which are configured to accept the male threads 20a of the insertion tool 20. The insertion tool 20 may be formed of any substantially rigid material, but preferably is formed of a material that is bio-compatible such as titanium, stainless steel, nickel, or of a bio-compatible alloy, composite, polymeric material or the like. It should be noted that the material of construction of the insertion tool could be any material without diverging from the broad scope of the present invention. It is also contemplated that the insertion tool 20 and vertebral defect device 10 may be releasably coupled by any of several releasable fastening mechanisms known to those skilled in the art.

Figure 16A:
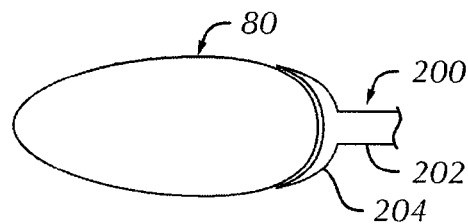
FIG. 16A is a left side elevational view of a second preferred embodiment of an insertion tool for a vertebral defect device in accordance with the present invention.
Figure 16B:
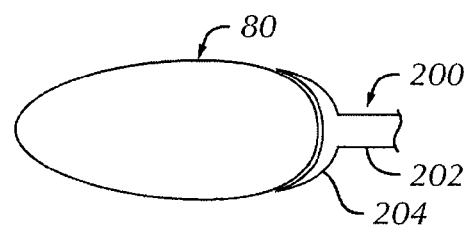
FIG. 16B is a top plan view of the insertion tool of FIG. 16A.

FIGS. 16A-16B show a second preferred embodiment of an insertion tool 200 for a vertebral defect device 10, 70, 80, 90, or 190 in accordance with the present invention. The insertion tool 200 has an elongate handle 202 and a grip 204. The grip 204 may be a suction cup or other similar gripping-type mechanism.

Figure 3:
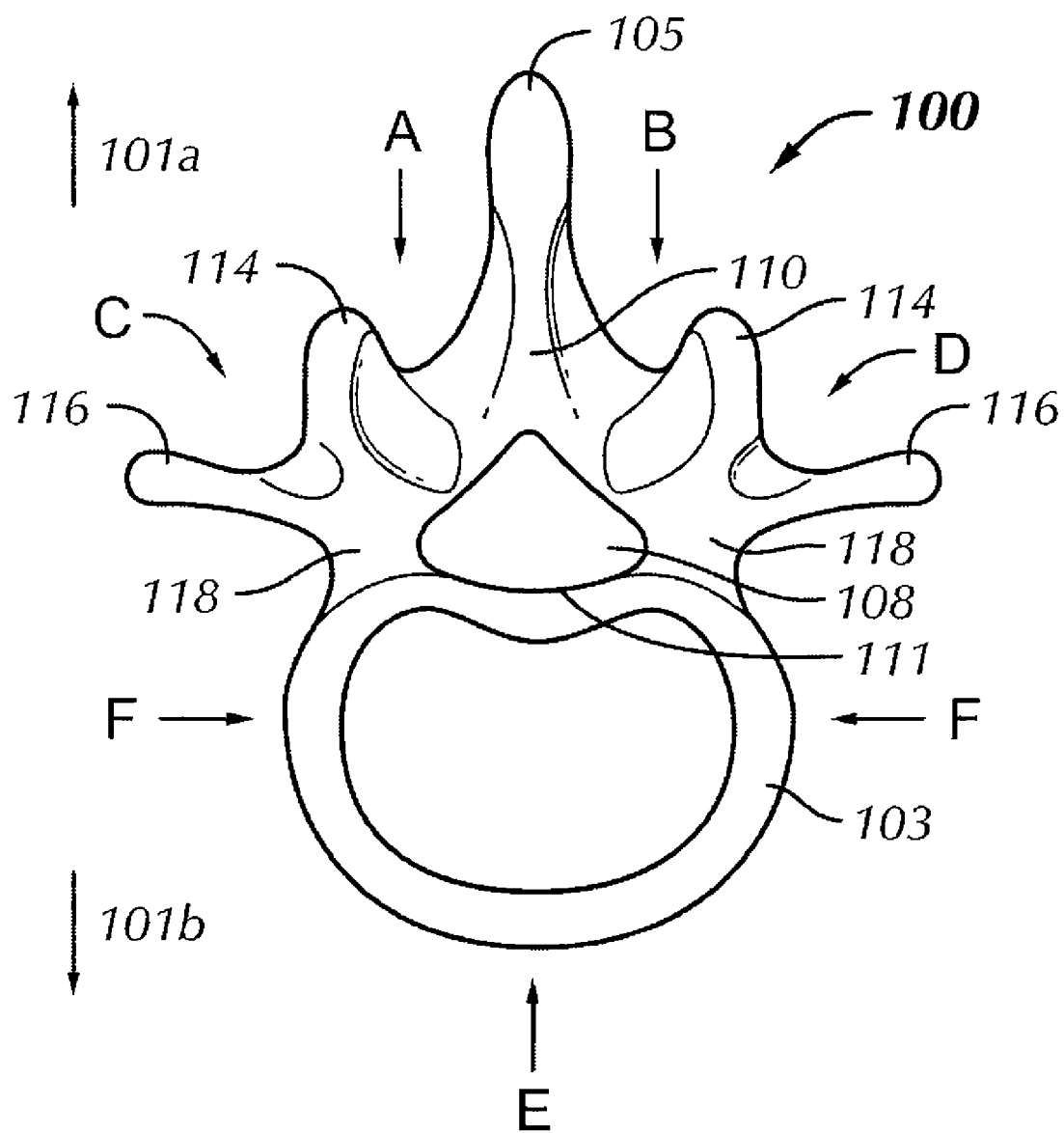
FIG. 3 is a top plan view of a human vertebra as is known in the art.
Figure 4:
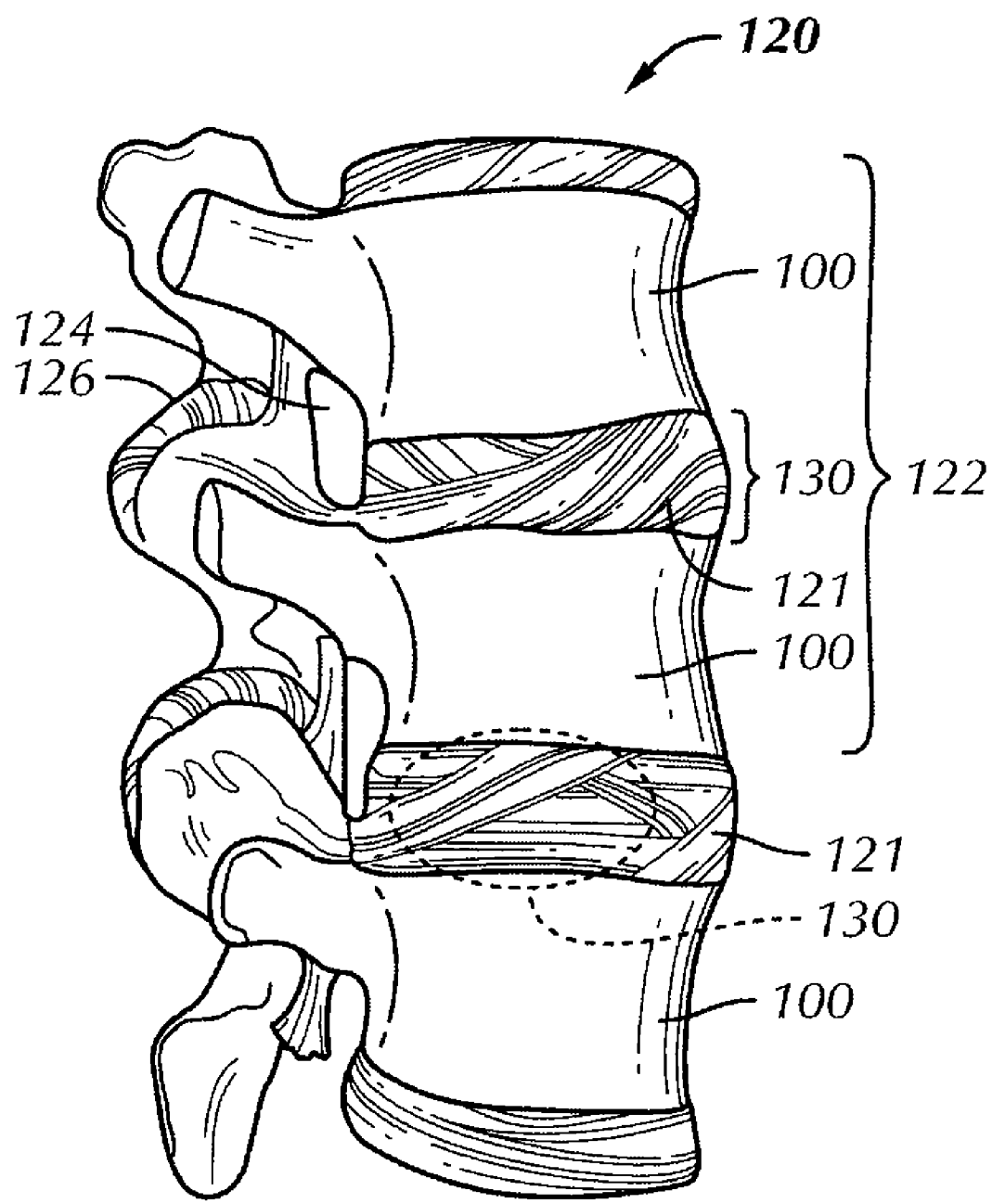
FIG. 4 is a right side elevation view of a portion of the lumbar spine as is known in the art.
Figure 12:
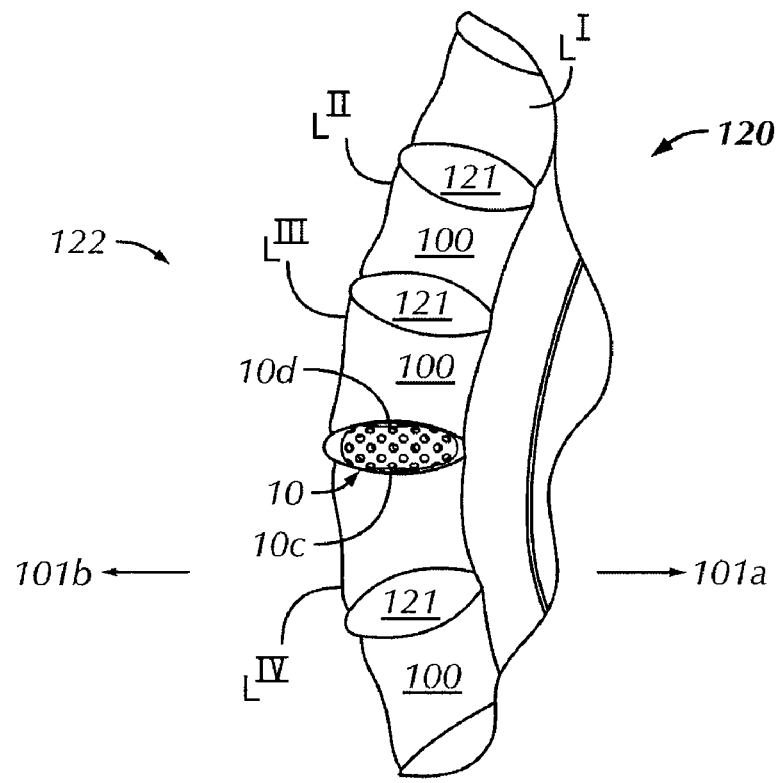
FIG. 12 is a left side view of the vertebral defect device of FIG. 5 installed between lumbar vertebrae $L^{III}$ and $L^{IV}$v.

FIG. 12 shows a side view of the lumbar region 122 of a portion of a human spine 120. In particular, a vertebral defect device 10 in accordance with the first preferred embodiment of the present invention is shown installed between lumbar vertebra $L^{III}$ and lumbar vertebra $L^{IV}$. In this particular installation, the second sidewall 10f of the vertebral defect device 10 is placed on the anterior side of the $L^{III}$-$L^{IV}$ intervertebral space, the first sidewall 10e of the vertebral defect device 10 is placed closest to the posterior side of the $L^{III}$-$L^{IV}$ intervertebral space, the upper wall 10d of the vertebral defect device 10 is adjacent to vertebra $L^{III}$, and the lower wall 10c of the vertebral defect device 10 is adjacent to vertebra $L^{IV}$. In this example, the surgeon would have inserted the distal end 10a of the vertebral defect device 10 into the gap between the $L^{III}$-$L^{IV}$ vertebrae as depicted in FIG. 3 by a directional arrow D. It is just as likely and possible for the surgeon to place the distal end 10a of the vertebral defect device 10 through the space between the $L^{III}$-$L^{IV}$ vertebrae in the direction of a directional arrow C (FIG. 3) or from other directions.

Figure 9:
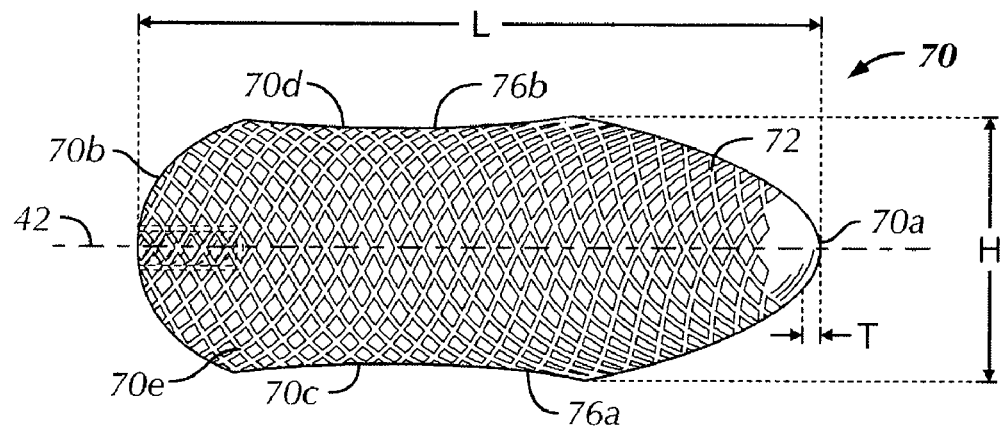
FIG. 9 is a side elevational view of a second preferred embodiment of a vertebral defect device in accordance with present invention.

FIG. 9 shows a side elevational view of a second preferred embodiment of a vertebral defect device 70 in accordance with the present invention. The intervertebral defect device or vertebral defect device 70 has a distal end 70a, a proximal end 70b, a lower wall 70c, an upper wall 70d, a first sidewall 70e, and a second sidewall (not shown). An outer surface 72 differs from the first preferred embodiment only in that the outer surface 72 of the vertebral defect device 70 is a lattice-type structure, instead of the body having a plurality of apertures 11, but the outer surface 72 is also substantially smooth with rounded edges and can be made from similar materials as described with reference to the first preferred embodiment. In an alternate embodiment of the second preferred embodiment of the vertebral defect device 70, the lower wall 70c defines a lower opening 76a and the upper wall 70d defines an upper opening 76b at the point of vertebral contact to encourage successful fusion.

Figure 10A:
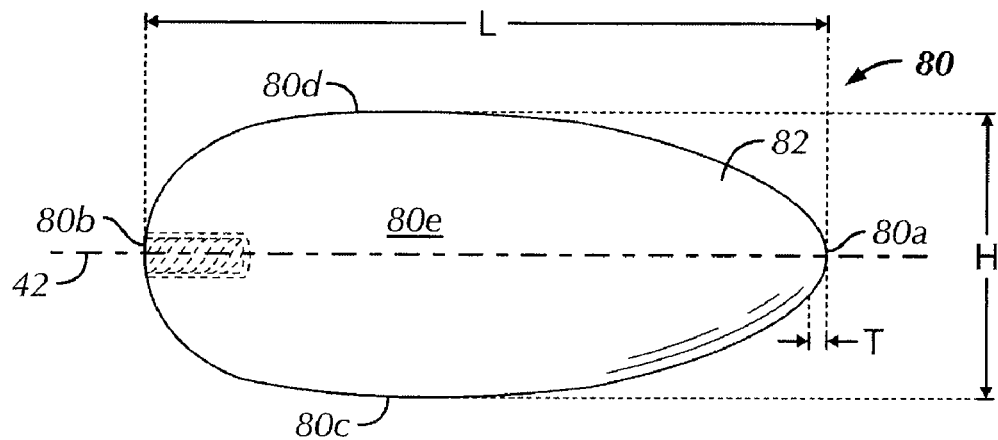
FIGS. 10A-10B are side elevational views of a third preferred embodiment of a vertebral defect device in accordance with present invention.
Figure 10B:
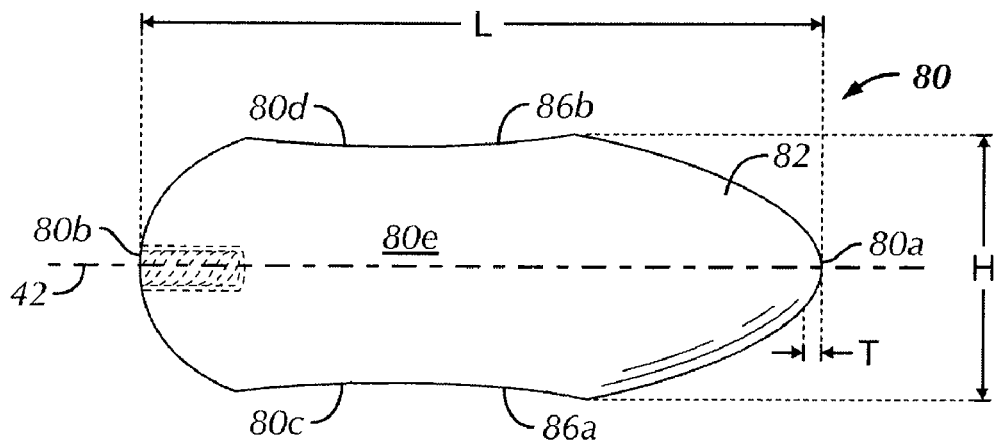

FIGS. 10A-10B show a third preferred embodiment of a vertebral defect device 80 in accordance with the present invention. FIG. 10A shows that the vertebral defect device 80 has a distal end 80a, a proximal end 80b, a lower wall 80c, an upper wall 80d, a first sidewall 80e, and a second sidewall (not shown). The vertebral defect device 80 further has an outer surface 82, which in the present embodiment, is substantially smooth and free from apertures, openings, and the like. The presently preferred embodiment is ideally suited for use as a disk prosthesis or nuclear replacement-type device due to the lack of openings. It would be obvious to one skilled in the art to form the vertebral defect device 80 out of a material that would not encourage adhesion or bone or tissue growth. Optionally, as shown in FIG. 10B, when the vertebral defect device 80 is applied as a fusion device, the lower wall 80c defines a lower opening 86a and the upper wall 80d defines an upper opening 86b for intervertebral contact to encourage successful fusion.

Figure 13:
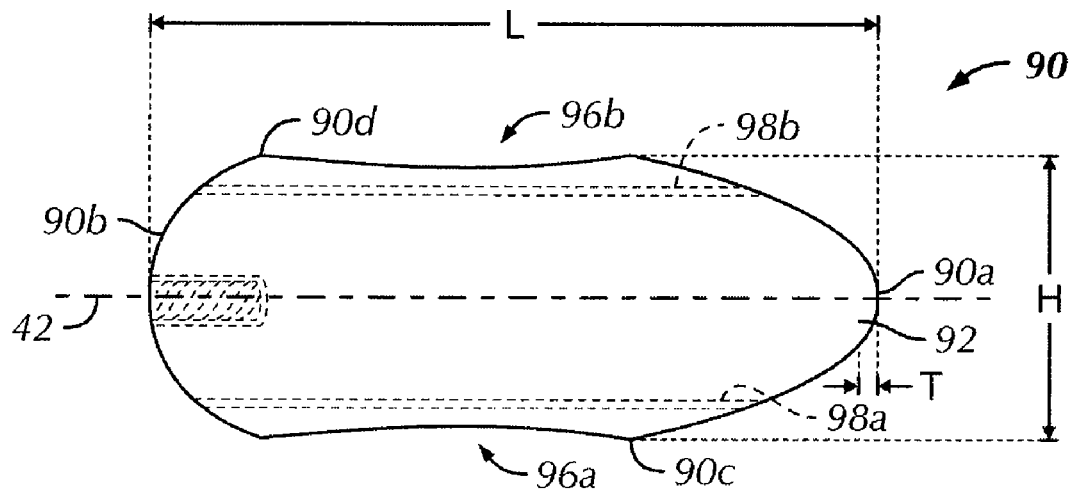
FIG. 13 is a right side elevational view of a fourth preferred embodiment of a vertebral defect device in accordance with the present invention.
Figure 14:
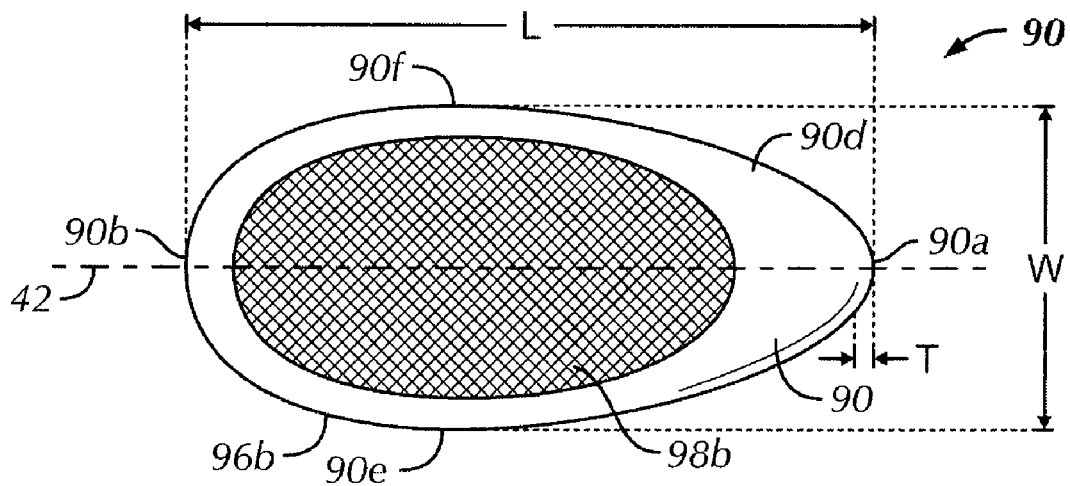
FIG. 14 is a top plan view of the vertebral defect device of FIG. 13.

FIGS. 13 and 14 show a fourth preferred embodiment of a vertebral defect device 90 in accordance with the present invention. The vertebral defect device 90 has a distal end 90a, a proximal end 90b, a lower wall 90c, an upper wall 90d, a first sidewall 90e, and a second sidewall 90f. The vertebral defect device 90 further has an outer surface 92, which in the present embodiment, is substantially smooth and free from apertures, openings, and the like, but may have apertures without departing from the present invention. The lower wall 90c defines a lower opening 96a and the upper wall 90d defines an upper opening 96b for intervertebral contact to encourage successful fusion. The vertebral defect device 90 further includes a lower grating 98a and an upper grating 98b. Preferably, the gratings 98a, 98b are formed of a substantially rigid mesh that is coated with a bio-compatible ceramic to promote bone growth. The gratings 98a, 98b are located slightly below an outer edge defined by the openings 96a, 96b in order to allow some or partial subsidence of the vertebrae 100 partially into the vertebral defect device 90, but will prevent excessive subsidence. It has been contemplated that in lieu of openings 96a, 96b, the gratings 98a, 98b are merely recessed portions of the lower wall 90c and upper wall 90d having perforations, apertures or slits which allow bone ingrowth.

Figure 15A:
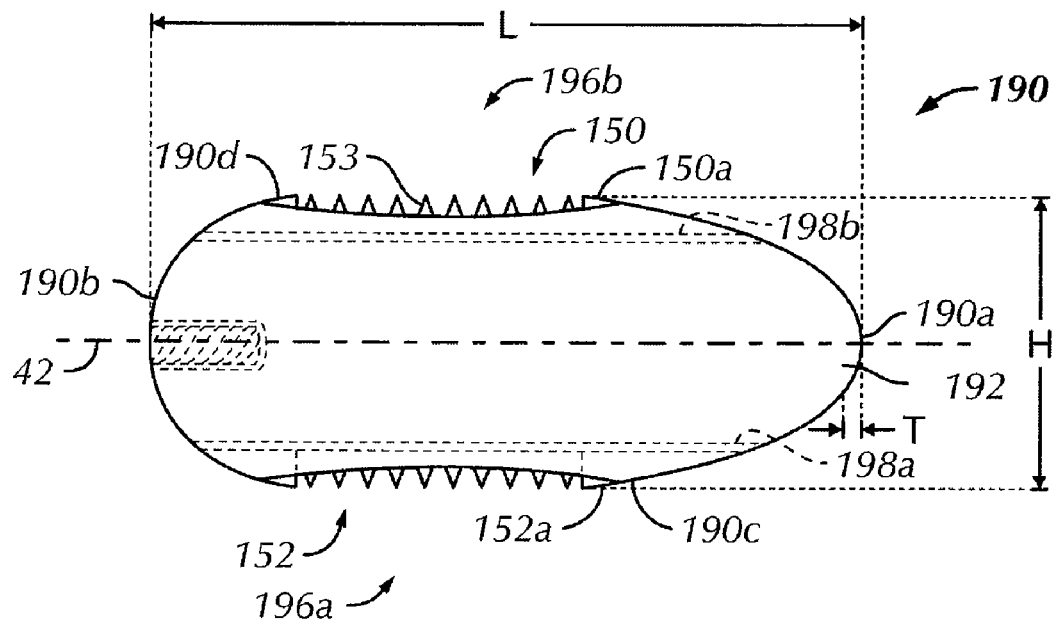
FIG. 15A is a right side elevational view of a fifth preferred embodiment of a vertebral defect device in accordance with the present invention.
Figure 15B:
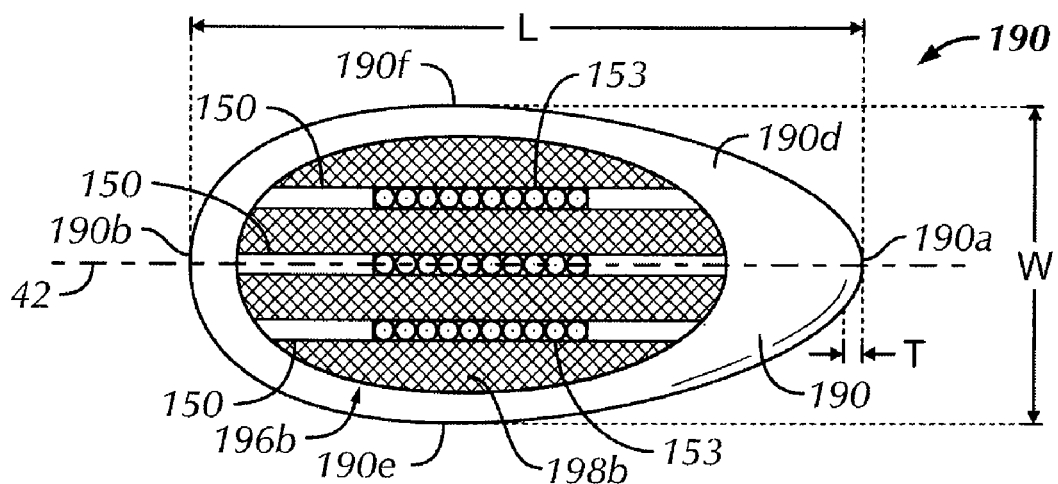
FIG. 15B is a top plan view of the vertebral defect device of FIG. 15A.

FIGS. 15A and 15B show a fifth preferred embodiment of a vertebral defect device 190 in accordance with the present invention. The vertebral defect device 190 has a distal end 190a, a proximal end 190b, a lower wall 190c, an upper wall 190d, a first sidewall 190e, and a second sidewall 190f. The vertebral defect device 190 further has an outer surface 192, which in the present embodiment, is substantially smooth and free from apertures, openings, and the like, but may have apertures without departing from the present invention. The lower wall 190c defines a lower opening 196a and the upper wall 190d defines an upper opening 196b for intervertebral contact to encourage successful fusion. The vertebral defect device 190 further includes a lower grating 198a and an upper grating 198b. Preferably, the gratings 198a, 198b are formed of a substantially rigid mesh that is coated with a bio-compatible ceramic to promote bone growth. The gratings 198a, 198b are located slightly below an outer edge defined by the openings 196a, 196b in order to allow some subsidence of the vertebrae 100 partially into the vertebral defect device 190, but will prevent excessive subsidence.

Further, the vertebral defect device 190 includes at least one upper arch 150 and at least one lower arch 152, but preferably the vertebral defect device 190 includes three upper arches 150 and three lower arches 152. The arches 150, 152 are generally disposed symmetrically along and about a centerline of the longer axis of the vertebral defect device 190 and are secured to the body of the vertebral defect device 190. Of course the arches 150, 152 may be secured to the vertebral defect device 190 by other means and may be disposed in other orientations without departing from the spirit of the present invention. Preferably, the arches 150, 152 protrude above the top and bottom 190d, 190c of the vertebral defect device 190, respectively. The arches 150, 152 are configured to settle into bone matter, and therefore, the arches 150, 152 have sharpened edges 150a, 152a. The sharpened edges 150a, 152a may include serrations, pins, sharpened cones or a simple knife-like edge, but need not be. Preferably, the sharpened edges 150a, 152a are partially knife like proximate the ends of the arches and partially covered with sharpened cones 153. The arches 150, 152 are preferably about 0.5 mm to about 2.0 mm wide. The arches 150, 152 also serve to center the vertebral defect device 190 during placement and prevent the vertebral defect device from rolling or canting thereafter.

It should be obvious to one skilled in the art that arches 150, 152 could be utilized in any of the embodiments of the vertebral defect devices 10, 70, 80, 90, or 190, as described herein.

Figure 17A:
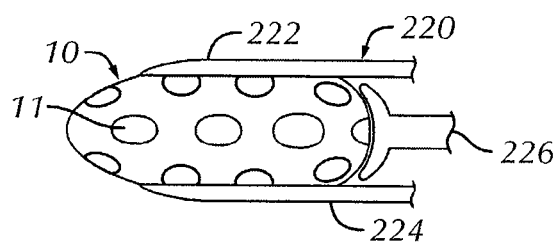
FIG. 17A is a left side elevational view of a third preferred embodiment of an insertion tool for a vertebral defect device in accordance with the present invention.
Figure 17B:
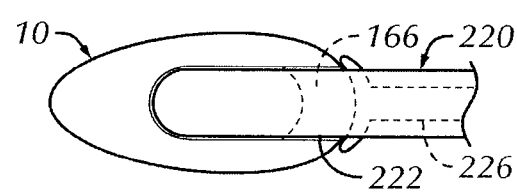
FIG. 17B is a top plan view of the insertion tool of FIG. 17A.

FIGS. 17A-17B show a third preferred embodiment of an insertion tool 220 for a vertebral defect device 10 (70, 80, or 90) having upper and lower openings 16a, 16b (76a, 76b, 86a, 86b, 96a, 96b). The insertion tool 220 has a first finger 222 configured to cooperatively engage the upper opening 16a and a second finger 224 configured to cooperatively engage the lower opening 16b. The fingers 222, 224 have outer surfaces which are shaped to match the contoured shape of the vertebral defect device 10 to allow a smooth insertion of the vertebral defect device 10. The combination of the insertion tool 220 and the vertebral defect device 10 when the first and second fingers 222, 224 are engaged with the ingrowth openings 16a, 16b, forms a combined structure having generally rounded exposed surfaces. The fingers 222, 224 also prevent foreign matter and debris from getting caught in the openings 16a, 16b during insertion. Because the fingers 222, 224 grasp the vertebral defect device 10 in a specific orientation defined by the upper and lower openings 16a, 16b, the insertion tool 220 provides the surgeon with means to orient the vertebral defect device 10 correctly during insertion.

The insertion tool 220 further includes a driving member 226 that is configured to engage the body of the vertebral defect device 10. The driving member 226 is configured to be impacted such that during insertion a surgeon may tap or hammer the driving member 226 to push the vertebral defect device 10 through a small opening. Preferably, the first and second fingers 222, 224 are retractable relative to the driving member 226. Thus, after the defect device 10 is inserted to a desired position, the first and second fingers 222, 224 are retracted while the driving member 226 holds the defect device 10 in place. Optionally, the vertebral defect device 10 may have grooves 166 (shown in phantom in FIG. 17B) extending from the upper and lower openings 16a, 16b to facilitate the removal of the retractable fingers 222, 224.

Figure 18A:
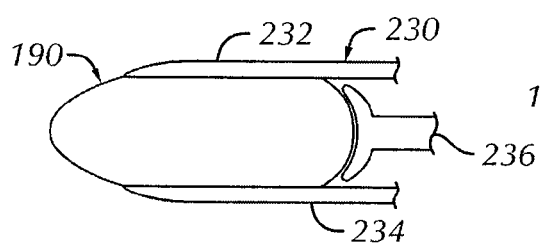
FIG. 18A is a left side elevational view of a fourth preferred embodiment of an insertion tool for a vertebral defect device in accordance with the present invention.
Figure 18B:
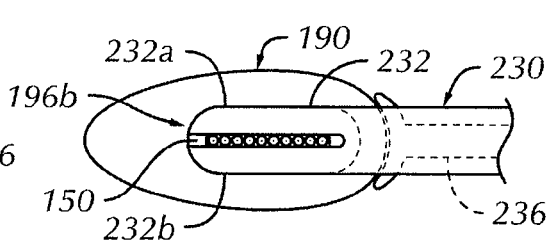
FIG. 18B is a top plan view of the insertion tool of FIG. 18A.

FIGS. 18A-18B is a side elevational view of a fourth preferred embodiment of an insertion tool 230 for a vertebral defect device 190 having lower and upper openings 196a, 196b and upper and lower arches 150, 152. For example, the upper finger 232 has first and second prongs 232a, 232b for straddling the upper arch 150 as best seen in FIG. 18. The insertion tool 230 is similar to the insertion tool 220, but each of the retractable fingers 232 234 is forked to accommodate the arches 150, 152. Preferably, the arches 150, 152 are just below the outer surface of the fingers 232, 234, so that the arches 150, 152 do not injure adjacent tissue during insertion. Furthermore, it would be obvious to one skilled in the art to utilize multiple prongs 232a, 232b in each of the retractable fingers 232, 234 in order to accommodate multiple arches 150, 152.

The vertebral defect device 10 has a maximum height H and/or maximum width W, preferably in the range of 6 to 16 mm, at an axial location intermediate the distal end 10a and the proximal end 10b. The vertebral defect device 10 has a length L, preferably in the range of 10 to 30 mm, along a longitudinal axis 42. An outer profile of the vertebral defect device 10 is characterized by a relatively gradual slope, such that the diameter (height and width) of the vertebral defect device 10 preferably changes no more than about 2 mm for every 1 mm change in length. Preferably, the distal end 10a, in particular, has a slope that changes by no more than about 2 mm for every 1 mm change in length. The distal end 10a is preferably relatively small, for example, less than 2.5 mm in diameter over the terminal 1 mm T of the distal end 10a along the longitudinal axis 42 or approximately 5-20% of the maximum height H and/or maximum width W of the vertebral defect device 10. However, the distal end 10a should not be so pointed such that it would easily drive through or penetrate the opposite side of the annulus on the opposite side of the disk space. The taper and slope of the distal end 10a of the vertebral defect device 10 permit the vertebral defect device 10 to be at least partially self-distracting. Generally, the vertebral defect device 10 is intended to be impacted into the disk space while providing such distraction of the periphery of the vertebral bodies 100 to permit entry into the nuclear center of the disk. The vertebral defect device 10 may be dimensioned in accordance with the requirements of specific applications, and other dimensional characteristics of the vertebral defect device 10 are included within the scope of this invention.

Figure 19:
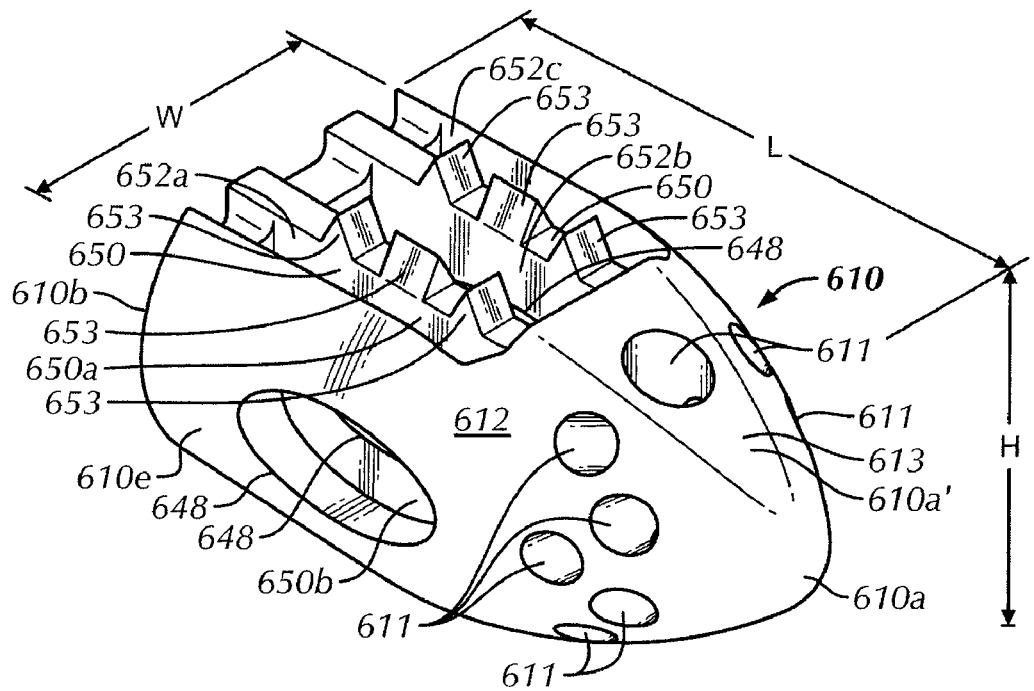
FIG. 19 is a top perspective view of a six preferred embodiment of a vertebral defect device in accordance with the present invention.
Figure 20:
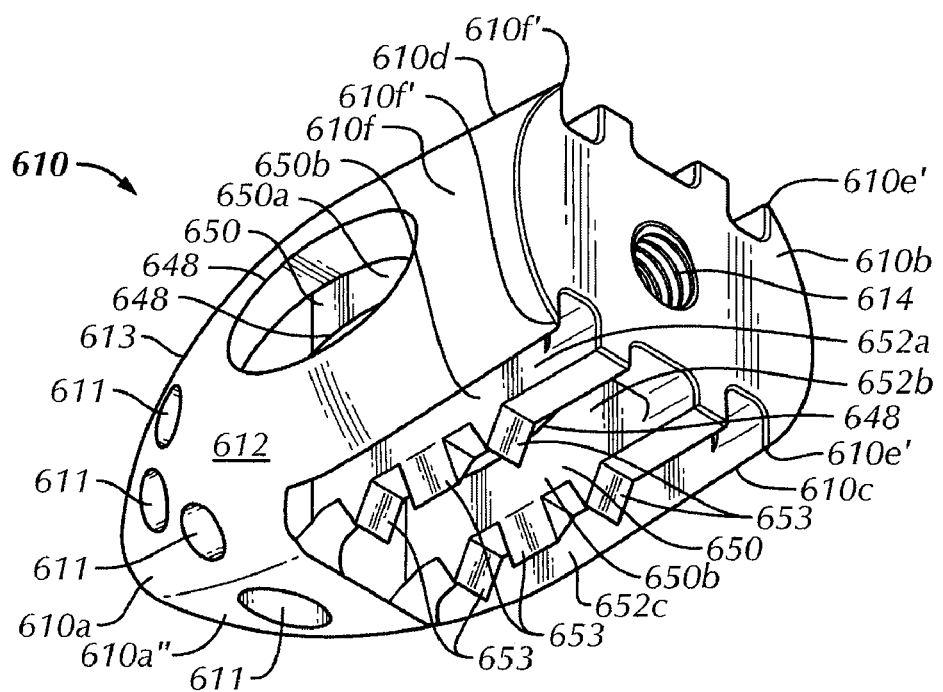
FIG. 20 is a bottom perspective view of the vertebral defect device of FIG. 19.
Figure 21:
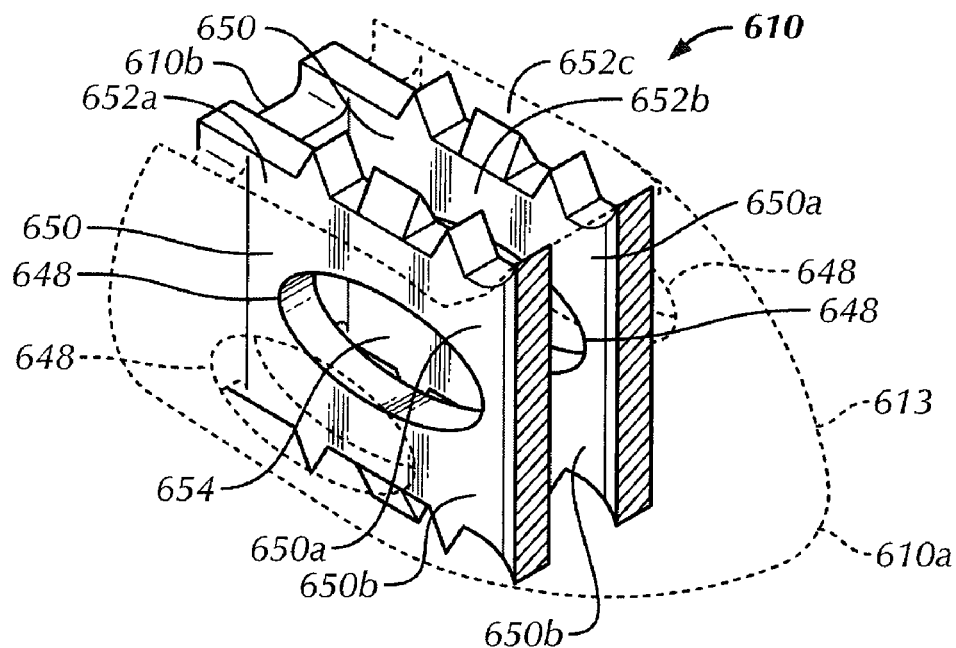
FIG. 21 is a partially transparent perspective view of the vertebral defect device of FIG. 19 showing the supports.

Referring to FIG. 19-21, there is shown a sixth preferred embodiment of a vertebral defect device, generally designated 610. The vertebral defect device 610 has a rigid body 613 which has a tapered, closed insertion end, distal tip or distal end 610*a*, a proximal end 610*b*, a bottom 610*c*, a top 610*d*, a first lateral side or sidewall 610*e* (FIG. 19) and a second lateral side or sidewall 610*f* (FIG. 20). The rigid body 613 preferably has an outer surface 612 that is substantially smooth over the entire surface of the rigid body 613. The vertebral defect device 610 is preferably constructed entirely of a single material, such as surgical grade titanium that is discernable by electromagnetic imaging, such as x-rays and computed tomography (CT) scans, but has minimal interference with magnetic resonance imaging (MRI) scans. The vertebral defect device 610 may be constructed of any material selected from the group consisting of a biocompatible material such as machined bone, stainless steel, titanium, a cobalt-chrome alloy, a nickel plated metal, a biocompatible alloy, a biocompatible ceramic, a biocompatible polymeric material or a biologically absorbable material. Though the above materials are preferred, any material allowing adequate support strength that could be machined, milled and/or assembled into the shapes and features disclosed below could be used to form the vertebral defect device.

The vertebral defect device 610 is generally egg-shaped or ovoid-shaped with rounded or contoured edges on all of the surfaces exposed during insertion. An outer profile of the vertebral defect device 610 is characterized by a relatively gradual slope, such that the largest transverse dimension (height H or width W) of the vertebral defect device 610 preferably changes no more than about 2 mm for every 1 mm change in length. Preferably the distal end 610*a*, in particular, has a slope that changes by no more than 2 mm for every 1 mm change in length. The distal end 610*a* preferably comes to a generally blunt tip with a top surface 610*a*' and a bottom surface 610*a*" that preferably have a longitudinal taper and convexity but no lateral convexity to provide a flat longitudinal surface for contacting the adjacent vertebrae 100 during insertion. The distal end 610*a* is preferably 2.5 mm or less in a vertical or transverse dimension over the terminal 1 mm of the distal end 610*a* along the length L or approximately 15-20% of the maximum height H or maximum width W of the vertebral defect device 610. The distal end 610*a* is preferably bluntly pointed such that it would not easily drive through or penetrate the annulus on the opposite side of the intervertebral disk space 130 during insertion.

The distal end 610*a* preferably includes a plurality of apertures 611 extending entirely therethrough. The apertures 611 are intended to promote rapid bone ingrowth while the vertebral defect device 610 maintains a stiff support structure between the vertebrae 100 during insertion and the bone growth process. The apertures 611 preferably intersect at a central hub (not shown) such that the apertures are all interconnected. However, the apertures 611 need not intersect or overlap. The apertures 611 are preferably circular in shape since it is easier to drill a circular hole. However, the apertures 611 may be any shape including ovals, squares, rectangles, triangles, diamonds, crosses, X-shapes, and the like. Additionally, the distal end 610*a* need not include any apertures 611.

The first and second lateral sidewalls 610*e*, 610*f* extend proximally from the distal end 610*a*. Spaced between the first and second lateral sidewalls 610*e*, 610*f* is at least one and preferably two supports 650. Though it is preferred that the vertebral defect device 610 include two supports 650, the vertebral defect device 610 may include any number of supports 650. The supports 650 are preferably generally planar and extend from the top 610*d* to the bottom 610*f* for providing a rigid support between adjacent vertebrae 100. The supports 650 are preferably generally parallel to each other and to the lateral sidewalls 610*e*, 610*f* and extend generally along the length L or from the distal end 610*a* toward the proximal end 610*b*. However, the supports 650 may extend at an angle and/or form a cross. Having the supports 650 extend generally along the length L rather than the width W permits a larger interior space for the bone matter as described further below. A first space or slot 652*a* is preferably formed between the first lateral sidewall 610*e* and one of the supports 650, a second space or slot 652*b* is preferably formed between the supports 650 and a third space or slot 652*c* is preferably formed between one of the supports 650 and the second lateral sidewall 610*f*. Preferably, at least a portion of the first, second and third slots 652*a*, 652*b*, 652*c* extends entirely through the vertebral defect device 610 to allow for bone growth out of, in and through the vertebral defect device 610.

Each of the supports 650 preferably includes at least one partially sharpened edge or projection 653 extending outwardly therefrom proximate the top and bottom 610*d*, 610*c*. The projections 653 are preferably conically or triangularly shaped and project outwardly from the supports 650 by a predetermined distance. Alternatively, the projections 653 may slant toward the proximal end 610*b* for insertion purposes. The projections 653 are disposed at generally equally spaced intervals along each of the respective supports 650. The projections 653 each act as a barb and assist with securely retaining the vertebral defect device 610 in between a pair of vertebrae 100. Once the vertebral defect device 610 is correctly in place and the fingers 522, discussed below, are removed, the projections 653 penetrate into the bone of the adjacent vertebrae 100 to resist motion of the vertebral defect device 610 with respect to the adjacent vertebrae 100. Additionally, the first and second lateral sidewalls 610*e*, 610*f* preferably include sharpened edges 610*e*', 610*f*' (labeled in FIG. 20) that project outwardly from the vertebral defect device 610 and extend from the proximal end 610*b* toward the distal end 610*a*. The sharpened edges 610*e*', 610*f*' provide for rapid fixation of adjacent vertebral bodies 610 thus achieving instant stabilization. Though a combination of conical and triangular projections 653 as shown are preferred, the projections 653 may have any shape and may or may not be included on each or any support 650. Any number of projections 653 or sharpened edges 610*e*', 610*f*' may be made in any number of sizes or shapes, and may be placed in any number of arrangements, so long as the requisite retaining and fixation function is achieved. In particular, the projections 653 as well as the shape and orientation of the remaining features are shaped and arranged in ways that impart to the device a readily identifiable unique pattern when imaged after placement in the human body.

The first and second lateral sidewalls 610*e*, 610*f* preferably each include a side aperture 648 which preferably is one continuous opening that extends through the entire vertebral defect device 610 such that the side aperture 648 extends through the first lateral sidewall 610*e*, through the first slot 652*a*, through one of the supports 650, through the second slot 652*b*, through one of the supports 650, through the third slot 652*c* and through the second lateral sidewall 610*f*. However, the side aperture 648 may be comprised of two or more separate or differently sized openings. The side aperture 648 preferably forms or is connected to a central cavity 654 (FIG. 21). The side aperture 648 and/or central cavity is sufficiently sized to allow for the insertion of bone growth material. The side aperture 648 also allows for viewing of the bone growth between the adjacent vertebrae 100 using an imaging device. Growing bone (not shown) can then extend through the first, second and third slots 652a, 652b, 652c. The side aperture 648 and resulting central cavity 654 are preferably oval shaped with the larger width extending along the length L of the vertebral defect device 610 to maximize the shape of the side aperture 648 and central cavity 654. However, the side aperture 648 and/or central cavity 654 may have any suitable shape such as circular or square. Because the side aperture 648 extends through the general center of the supports 650, each support 650 may be considered to be or actually constructed of an upper arch 650a and a lower arch 650b. The upper and lower arches 650a, 650b may be separately or integrally formed so long as each support 650 provides strength in the vertical direction between the top 610d and the bottom 610c of the vertebral defect device 610 to prevent subsidence while the central cavity 654 and the fusion material and the growing bone is shielded during the healing or fusion process.

Though it is preferred that the supports 650 have a planar or plate-like shape, the supports 650 may have any shape that allows for a vertical opening through vertebral defect device 610 for facilitating intervertebral bone growth but also provides sufficient vertical strength. For example, bridges or connectors (not shown) may extend between the supports 650 and/or between the supports 650 and one of the lateral sidewall 610e, 610f.

The proximal end 610b preferably connects the first and second lateral sidewalls 610e, 610f and the supports 650 and at least partially confines the first, second and third slots 652a, 652b, 652c between the distal end 610a and the proximal end 610b. Alternatively, the proximal end 610b may be generally open such that the first, second and third slots 652a, 652b, 652c are open toward the proximal end 610b. The proximal end 610b is preferably generally planar to aid in connection to the insertion tool 520 as described further below but the proximal end 610b may have any suitable shape such as rounded. The proximal end 610b, or the portion of the vertebral defect device 610 toward the proximal end, though having a planar terminal end, is preferably tapered in the vertical direction between the top 610d and the bottom 610c giving the top 610d and bottom 610c, along with the taper and convexities of the other surfaces, a general convexity in order to cooperatively mate within the natural concavities of adjacent vertebral bodies 100. The taper of the distal end 610a diminishes more gradually than the taper of the proximal end 610b. The first sidewall 610e and second sidewall 610f of the vertebral defect device 610 preferably are similarly convex for similar reasons and to facilitate installation of the vertebral defect device 610 into an intervertebral space 121. However, the first and second lateral sidewalls 610e, 610f may be any shape such as partially or entirely planar. In particular, a central portion of the first and second lateral sidewalls 610e, 610f may have a generally planar shape to provide a narrower width W or a more box-like device.

The proximal end 610b preferably includes a connector port 614 to temporarily and removably couple with an insertion tool 520 as described in further detail below. The connector port 614 is preferably a threaded hole but may also include any other structure for engaging with the insertion tool such as a socket, a detent, a hole a slot or the like.

The overall shape of the vertebral defect device 610 is also designed for insertion using minimally invasive techniques through a special portal or channel allowing a procedure to be implemented on an outpatient basis. The shape of the vertebral defect device 610 is ideally suited for smooth insertion through a small opening, and therefore, the vertebral defect device 610 is well suited for minimally invasive and/or outpatient procedures. Further, the vertebral defect device 610 is a self centering device because the overall shape of the vertebral defect device 610 encourages the vertebral defect device 610 to settle within the natural concavities of adjacent vertebral bodies 100. As such, placement of the vertebral defect device 610 is much faster than that of prior art devices, thereby effectively reducing the duration of a procedure and the associated risks therewith. The smooth contour and edges of the vertebral defect device 610 provide for a safe and easy entrance into the intervertebral space 130.

The convex, bullet-like shape of the distal end 610a of the vertebral defect device 610 allows the vertebral defect device 610 to be driven into the intervertebral space 130 by merely temporarily distracting the vertebrae with minimal removal of the vertebral rim or annulus at the point of entry, thereby reducing the chance of dislodging the device post-surgery. Additionally, the self-centering feature of the vertebral defect device 610 allows rapid settling of the vertebral defect device 610 into adjacent bone to promote rapid bone ingrowth while retention of most of the annulus and peripheral rim of the vertebral bodies provides good load sharing support to prevent excessive subsidence, where subsidence results from the natural settling of intervertebral matter into a softer central portion of the vertebral bodies 103.

The size and taper or slope of the distal end 610a of the vertebral defect device 610 is intended to allow it to be impacted into the disk space 130 while providing distraction of the periphery of the vertebral bodies 103 to permit entry into the nuclear center of the disk. This minimizes a need to remove peripheral vertebral bone thus assisting with device retention and helps prevent potential extrusion of the vertebral defect device 610. The length L, width W and height H of the vertebral defect device 610 are preferably similar as described for the various embodiments above. However, the vertebral defect device 610 may be dimensioned in accordance with the requirements of specific applications. The vertebral defect device 610 is preferably machined or formed from a single rigid body however, the vertebral defect device 610 may be assembled from two or more segments or components. For example, the supports 650 are preferably formed by cutting out the slots 652a, 652b, 652c and the side aperture 648. However, the distal end 610a and the first and second lateral sidewalls 610e, 610f may be integrally formed to form the rigid body and the supports 650 may be snap fit or otherwise mounted between the first and second lateral sidewalls 610e, 610f. Alternatively, the vertebral defect device could be constructed of a lower and upper half that are mounted or fastened together.

Figure 23:
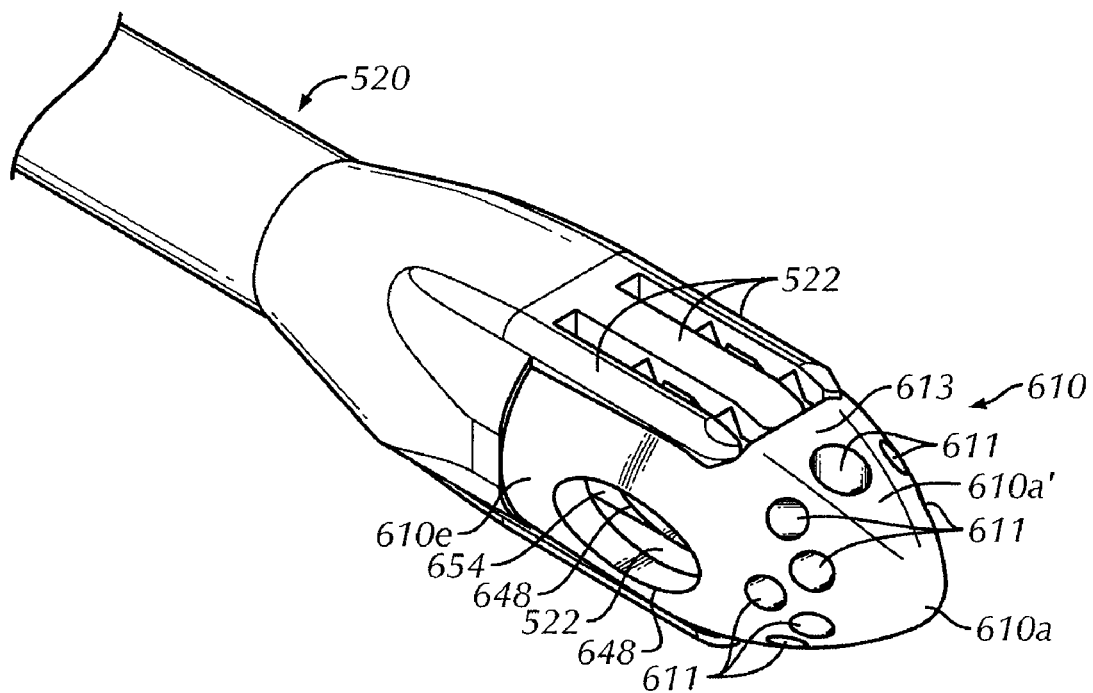
FIG. 23 is an enlarged perspective view of a distal end of the insertion tool mounted to the vertebral defect device as shown in FIG. 22.
Figure 22:
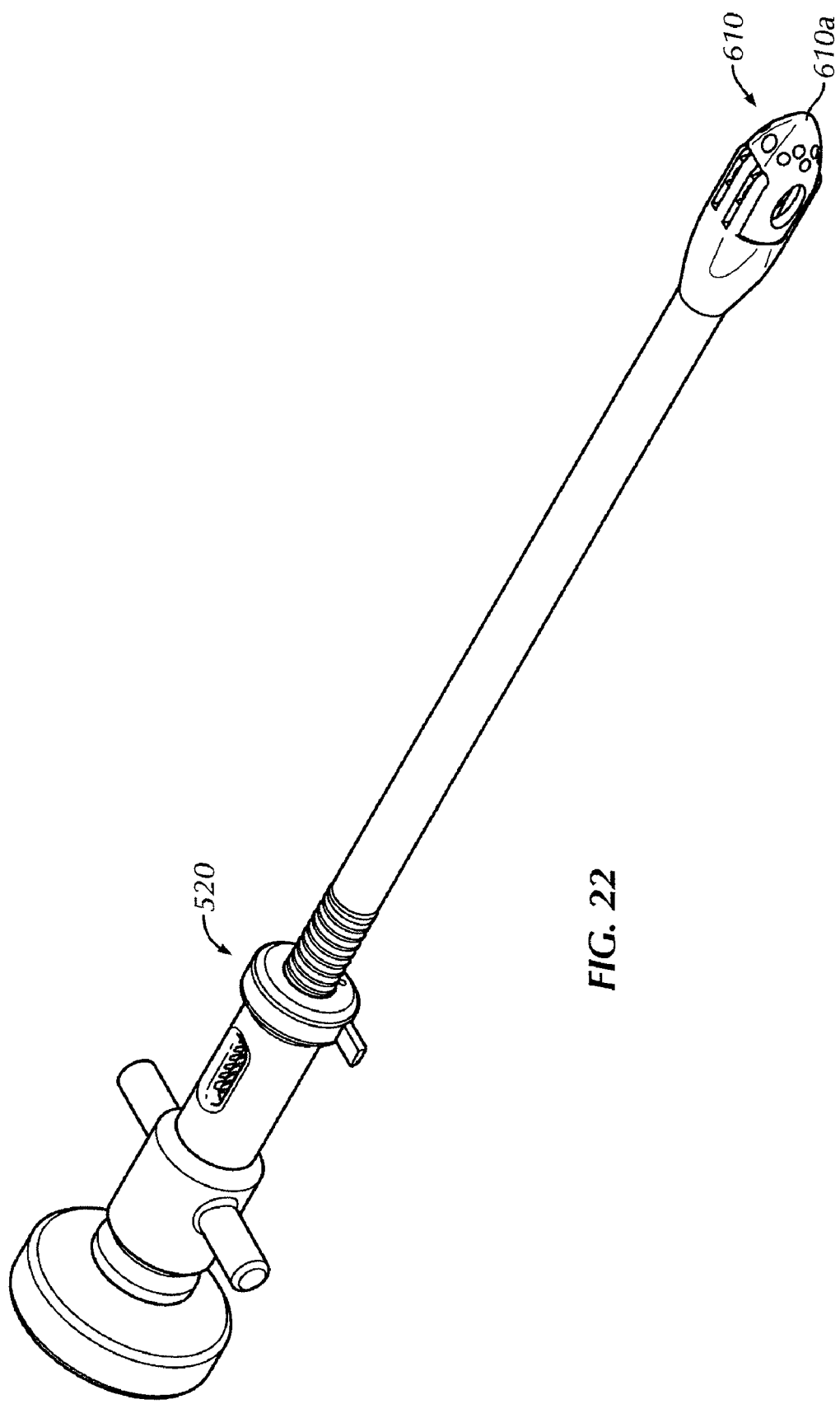
FIG. 22 is a perspective view of a fifth preferred embodiment of an insertion tool mounted to the vertebral defect device of FIG. 19.

FIGS. 22 and 23 show the vertebral defect device 610 of the sixth preferred embodiment with a fifth preferred embodiment of a specially designed insertion tool 520. The insertion tool 520 is threaded into the socket 614 in the proximal end 610b of the vertebral defect device 610. The socket 614 is provided with female threads 614 which are configured to accept the male threads (not shown) of the insertion tool 520. The insertion tool 520 may be formed of any substantially rigid material, but preferably is formed of a material that is bio-compatible such as titanium, stainless steel, nickel, or of a bio-compatible alloy, composite, polymeric material or the like. The insertion tool 520 preferably has a plurality of fingers 522 configured to cooperatively cover the first, second and third slots 652a, 652b, 652c and are shaped to match the contoured shape of the vertebral defect device 610 to allow a smooth insertion of the vertebral defect device 610. The combination of the insertion tool 520 and the vertebral defect device 610 when the fingers 522 are engaged with the first, second and third slots 652a, 652b, 652c forms a combined structure having generally rounded exposed surfaces. The fingers 522 also prevent foreign matter and debris from getting caught in the first, second and third slots 652a, 652b, 652c during insertion. After the defect device 610 is inserted to a desired position, the vertebral defect device 610 is released from the insertion tool 520 and the fingers 522 are removed.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

I claim:

1. A vertebral defect fusion device for insertion into an intervertebral space between a pair of adjacent vertebrae and assisting in fusion between the adjacent vertebrae, the vertebral defect device comprising:
    a rigid body having a closed distal end, a proximal end, a top, a bottom and a pair of lateral sides, the distal end forming a generally blunt tip, being tapered in a general direction that extends between the top and the bottom of the body to facilitate insertion of the body into the intervertebral space, and having a flat surface for contacting adjacent vertebrae during insertion, the proximal end connecting the lateral sides and having a connecting port for engaging an insertion tool;
    at least a first arch proximate the top of the body and extending from the proximal end of the body toward the distal end of the body, the first arch being spaced from both lateral sides of the body;
    at least a second arch proximate the bottom of the body and extending from the proximal end toward the distal end, the second arch being spaced from both lateral sides and generally laterally aligned with the first arch providing a rigid, generally vertical support, the first and second arches being joined to form said vertical support that is at least partially in the shape of a generally planar plate, at least a portion of the space between the support and one of the lateral sides extends entirely from the top of the body to the bottom of the body to provide an open gap between adjacent vertebrae;
    an aperture extending laterally through each of the lateral sides of the body and through each of the first and second arches to form at least a portion of a central cavity, the central cavity being sufficiently sized to receive material through the aperture for promoting bone growth in the central cavity through spaces between the first and second arches and between the arches and the lateral sides, the aperture being sufficiently large for viewing bone growth within the device; and
    a length of the device, as measured from the distal end to the proximal end of the rigid body, is greater than both a height of the device, as measured from the top to the bottom of the rigid body, and a width of the device, as measured from one lateral side to the opposing lateral side of the device, a maximum width of the device being different than a maximum height of the device,
    wherein the vertebral defect device is monolithically formed as a single piece and is generally egg-shaped with rounded or contoured edges on all exposed surfaces during insertion.

2. The vertebral defect device of claim 1, wherein the distal end is one of equal to and less than 2.5 mm in vertical height as measured between the top and bottom over a terminal 1 mm of the distal end.

3. The vertebral defect device of claim 1, wherein the distal end is about 5-20 percent of one of a maximum height of the body as measured between the top and the bottom and the maximum width as measured between the lateral sides.

4. The vertebral defect device of claim 1, wherein the distal end has a slope that changes no more than about 2 mm for every 1 mm change in length.

5. The vertebral defect device of claim 1, wherein one of the first and second arches includes at least one outwardly extending sharpened projection configured to promote fixation to one of the adjacent vertebrae.

6. The vertebral defect device of claim 1, wherein at least one of the pair of lateral sides include at least one linear sharpened edge that extends parallel to a longitudinal axis of the rigid body, the sharpened edge projects outwardly from the device and is formed at least in part by a vertically-extending surface and is configured to promote fixation to one of the adjacent vertebrae.

7. The vertebral defect device of claim 1 further comprising third and fourth arches forming a second support, the second support disposed between and at least partially spaced from the lateral sides.

8. The vertebral defect device of claim 1, wherein the distal end includes a plurality of apertures.

9. The vertebral defect device of claim 8, wherein the plurality of apertures extend entirely through the distal end and intersect one another.

10. The vertebral defect device of claim 1, wherein the top and bottom of the body are at least partially convexly shaped in order to cooperatively mate with concavities of the adjacent vertebrae.

11. The vertebral defect device of claim 1, wherein the lateral sides of the body are at least partially convexly shaped.

12. The vertebral defect device of claim 1, wherein the vertebral defect device is comprised entirely of a single material.

13. A vertebral defect fusion device for insertion into an intervertebral space between a pair of adjacent vertebrae and assisting in fusion between the adjacent vertebrae, the vertebral defect device comprising:
    a rigid body having a closed distal end, a proximal end, a top, a bottom and a pair of lateral sides, the distal end forming a generally blunt tip, being tapered in a general direction that extends between the top and the bottom of the body in order to facilitate insertion of the body into the intervertebral space, and having a flat surface for contacting adjacent vertebrae during insertion, the proximal end connecting the lateral sides and having a connecting port for engaging an insertion tool;
    at least two slots extending entirely through the body from the top to the bottom to provide an open gap between adjacent vertebrae and to form at least one rigid support at least partially in the shape of a generally planar plate disposed between and at least partially spaced from the lateral sides, the at least two slots having a length extending between the proximal and distal ends of the body and a width extending between the lateral sides, the length of each of the at least two slots being larger than the width of each slot;
    an aperture extending laterally through each of the lateral sides of the body, the rigid support and the at least two slots to form at least a portion of a central cavity, the central cavity being sufficiently sized to receive material through the aperture for promoting bone growth in the central cavity through the slots, the aperture being sufficiently large for viewing bone growth within the device;

a length of the device, as measured from the distal end to the proximal end of the rigid body, being greater than both a height of the device, as measured from the top to the bottom of the rigid body, and a width of the device, as measured from one lateral side to the opposing lateral side of the device, a maximum width of the device being different than a maximum height of the device; and a plurality of apertures extending entirely through the closed distal end of the rigid body and intersecting one another, wherein the vertebral defect device is monolithically formed as a single piece and is generally egg-shaped with rounded or contoured edges on all exposed surfaces during insertion.

14. The vertebral defect device of claim 13, wherein the vertebral defect device is comprised entirely of a single material.

15. A vertebral defect fusion device for insertion into an intervertebral space between a pair of adjacent vertebrae and assisting in fusion between the adjacent vertebrae, the vertebral defect device comprising:

a rigid body having a tapered, closed distal tip to facilitate insertion of the body into the intervertebral space, first and second lateral sidewalls spaced from each other and extending proximally from the distal tip, and a proximal end joining the lateral sidewalls to at least one support plate and at least partially confining first and second slots between the proximal end and the distal tip, the distal tip forming a generally blunt tip having a flat surface for contacting adjacent vertebrae during insertion;

the at least one support plate extending proximally from the distal tip of the body and spaced from and between the lateral sidewalls of the body to form the first slot between the first lateral sidewall and the at least one support plate and the second slot between the second lateral sidewall and the at least one support plate, at least one of the first and second slots extends entirely from a top of the body to a bottom of the body to provide an open gap between adjacent vertebrae;

an aperture extending laterally through both of the first and second lateral sidewalls and through the at least one support plate forming at least a portion of a central cavity, the central cavity being sufficiently sized to receive material through the aperture for promoting bone growth in the central cavity through the slots, the aperture being sufficiently large for viewing bone growth within the device; and a length of the device, as measured from the distal end to the proximal end of the rigid body, being greater than both a height of the device, as measured from the top to the bottom of the rigid body, and a width of the device, as measured from an exterior surface of the first lateral sidewall to an exterior surface of the second lateral sidewall of the device, a maximum width of the device being different than a maximum height of the device, wherein the vertebral defect device is monolithically formed as a single piece and is generally egg-shaped with rounded or contoured edges on all exposed surfaces during insertion.

16. The vertebral defect device of claim 15, wherein the vertebral defect device is comprised entirely of a single material.

* * * * *